United States Patent
Zheng et al.

(10) Patent No.: US 11,680,070 B2
(45) Date of Patent: Jun. 20, 2023

(54) THIENO[2,3-C]PYRIDAZIN-4(1H)-ONE DERIVATIVE AND APPLICATION THEREOF

(71) Applicant: MEDSHINE DISCOVERY INC., Jiangsu (CN)

(72) Inventors: Xiaoping Zheng, Shanghai (CN); Zhigan Jiang, Shanghai (CN); Haiying He, Shanghai (CN); Jie Li, Shanghai (CN); Zhen Gong, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 23 days.

(21) Appl. No.: 15/734,906

(22) PCT Filed: Jun. 5, 2019

(86) PCT No.: PCT/CN2019/090164
§ 371 (c)(1),
(2) Date: Dec. 3, 2020

(87) PCT Pub. No.: WO2019/233443
PCT Pub. Date: Dec. 12, 2019

(65) Prior Publication Data
US 2021/0238190 A1 Aug. 5, 2021

(30) Foreign Application Priority Data

Jun. 5, 2018 (CN) .......................... 201810570719.7
Sep. 5, 2018 (CN) .......................... 201811033469.X

(51) Int. Cl.
| | |
|---|---|
| C07D 495/04 | (2006.01) |
| A61P 1/16 | (2006.01) |
| A61P 3/04 | (2006.01) |
| A61P 3/06 | (2006.01) |
| A61P 3/10 | (2006.01) |
| A61P 17/10 | (2006.01) |
| A61P 35/00 | (2006.01) |
| A61K 31/522 | (2006.01) |

(52) U.S. Cl.
CPC .............. C07D 495/04 (2013.01); A61P 1/16 (2018.01)

(58) Field of Classification Search
CPC .. C07D 495/04; A61P 1/16; A61P 3/04; A61P 3/06; A61P 3/10; A61P 17/10; A61P 35/00; A61K 31/522
See application file for complete search history.

(56) References Cited

U.S. PATENT DOCUMENTS

2012/0010247 A1 1/2012 Kamata et al.
2016/0108060 A1 4/2016 Greenwood et al.

FOREIGN PATENT DOCUMENTS

| | | |
|---|---|---|
| CN | 105358152 A | 2/2016 |
| CN | 108368125 A | 8/2018 |
| WO | WO-2013071169 A1 | 5/2013 |
| WO | 2014-182950 A1 | 11/2014 |
| WO | WO-2017075056 A1 | 5/2017 |
| WO | WO-2017147161 A1 * | 8/2017 |

OTHER PUBLICATIONS

Meanwell, N.A., "Synopsis of some recent tactical application of bioisosteres in drug design." Journal of medicinal chemistry 54.8 (2011): 2529-2591.*
Harrison, S.,"Preliminary efficacy and safety of acetyl-CoA carboxylase inhibitor GS-0976 in patients with compensated cirrhosis due to NASH." Journal of Hepatology 68 (2018): S583.*
International Search Report and Written Opinion regarding International Application No. PCT/CN2010/073565, dated Sep. 6, 2019.
Extended European Search Report regarding Patent Application No. 19815304.1, dated Feb. 2, 2022.
Chinese Office Action regarding Patent Application No. 201980037798.8, dated Jan. 30, 2022.
Feb. 23, 2023 European Office Action issued in European Patent Application No. 19815304.1.

* cited by examiner

*Primary Examiner* — John M Mauro
(74) *Attorney, Agent, or Firm* — Harness, Dickey & Pierce, P.L.C.

(57) ABSTRACT

Disclosed are a thieno[2,3-c]pyridazin-4(1H)-one derivative as an ACC1 or ACC2 inhibitor and an application thereof in preparing a drug as an ACC1 or ACC2 inhibitor. In particular, disclosed is a compound represented by formula (II) or an isomer or pharmaceutically acceptable salt thereof.

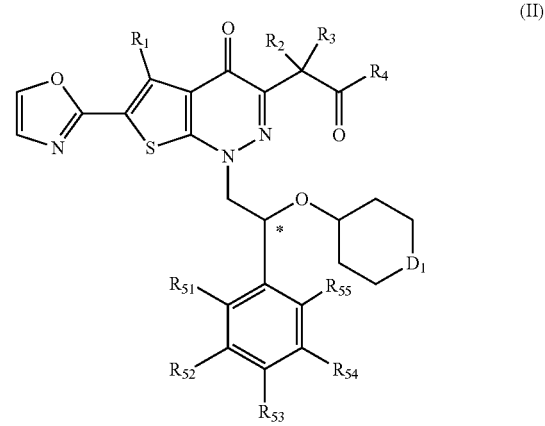

20 Claims, No Drawings

THIENO[2,3-C]PYRIDAZIN-4(1H)-ONE DERIVATIVE AND APPLICATION THEREOF

CROSS-REFERENCE TO RELATED APPLICATIONS

This application is a U.S. National Phase Application under 35 U.S.C. 371 of International Application No. PCT/CN2019/090164, filed Jun. 5, 2019, which claims the benefit of Chinese Patent Application No. CN 201811033469.X, filed Sep. 5, 2018 and Chinese Patent Application No. CN 201810570719.7, filed Jun. 5, 2018. The entire disclosures of the above applications are incorporated herein by reference.

TECHNICAL FIELD

The present disclosure relates to a thieno[2,3-c]pyridazin-4(1H)-one derivative as an ACC1 and ACC2 inhibitor, and a use thereof in the manufacture of a medicament as ACC1 and ACC2 inhibitor. Specifically, the present disclosure relates to a compound represented by formula (II), an isomer thereof or a pharmaceutically acceptable salt thereof.

BACKGROUND

Fatty acid metabolism disorders caused by increased fatty acid synthesis, decreased fatty acid oxidation, or the presence of both are signs of a variety of metabolic disorders, including insulin resistance, liver steatosis, dyslipidemia, obesity, metabolic syndrome (MetSyn), non-alcoholic fatty liver (NAFLD) and so on. Meanwhile, it may lead to the development of type 2 diabetes (T2DM), as well as non-alcoholic steatohepatitis (NASH), atherosclerosis and other vascular diseases. Fatty acid metabolism disorders are also a sign of cancer, which can lead to abnormal and persistent malignant tumor cell proliferation. Therefore, inhibiting the fatty acid synthesis and/or stimulating fatty acid oxidative metabolism may be beneficial to these diseases (PNAS, 2016, E1796-E1805).

Acetyl-CoA carboxylase (ACC) catalyzes the conversion of acetyl-CoA to malonyl-CoA, which is the first step in fatty acid synthesis and is also a rate-determining step. There are two subtypes of ACC, namely ACC1 and ACC2. ACC1 is mainly distributed in the liver and adipose tissue, while ACC2 is mainly distributed in liver, heart and muscle tissue. In the liver, the malonyl-CoA formed by catalysis of ACC1 in the cytoplasm is mainly responsible for the synthesis and elongation of fatty acids; the malonyl-CoA formed by catalysis of ACC2 on the surface of mitochondria is mainly responsible for the regulation of the oxidative metabolism of fatty acids by inhibiting carnitine transferase I (PNAS, 2016, E1796-E1805). Therefore, inhibiting the two subtypes of ACC simultaneously can reduce the synthesis of fatty acids and stimulate the oxidative metabolism of fatty acids.

WO2013071169A1 has disclosed the use of ACC inhibitor 1-181 in the treatment of related diseases.

I-181

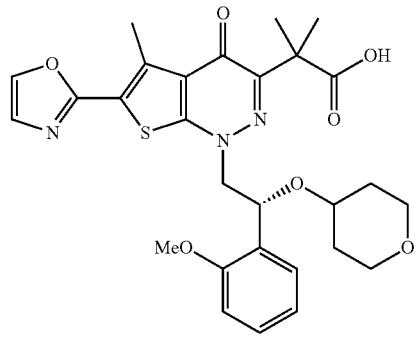

CONTENT OF THE INVENTION

The present disclosure provides a compound represented by formula (II), an isomer thereof or a pharmaceutically acceptable salt thereof, (II)

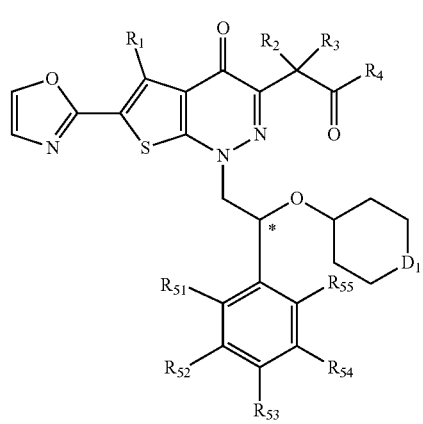

wherein, $D_1$ is selected from —O— and —N($R_6$)—;

$R_1$ is selected from H, F, Cl, Br, I, OH, $NH_2$ and $C_{1-3}$ alkyl, wherein the $C_{1-3}$ alkyl is optionally substituted by 1, 2 or 3 $R_a$;

$R_2$ is selected from H, F, Cl, Br, I, OH, $NH_2$ and $C_{1-6}$ alkyl, wherein the $C_{1-6}$ alkyl is optionally substituted by 1, 2 or 3 $R_b$;

$R_3$ is selected from H, F, Cl, Br, I and $C_{1-6}$ alkyl, wherein the $C_{1-6}$ alkyl is optionally substituted by 1, 2 or 3 $R_c$;

or, $R_2$ and $R_3$ are attached together to form a ring, the ring is selected from $C_{3-7}$ cycloalkyl and 4-7 membered heterocycloalkyl, the $C_{3-7}$ alkyl and 4-7 membered heterocycloalkyl are optionally substituted by 1, 2 or 3 $R_d$;

$R_4$ is selected from OH, $NH_2$, $C_{1-3}$ alkyl and $C_{1-3}$ alkylamino, wherein the $C_{1-3}$ alkyl and $C_{1-3}$ alkylamino are optionally substituted by 1, 2 or 3 $R_e$;

each of $R_{51}$, $R_{52}$, $R_{53}$, $R_{54}$ and $R_{55}$ is independently selected from H, F, Cl, Br, I, OH, $NH_2$, $C_{1-6}$ alkyl, $C_{1-6}$ alkylamino and $C_{1-6}$ alkoxy, wherein the $C_{1-6}$ alkyl, $C_{1-6}$ alkylamino and $C_{1-6}$ alkoxy are optionally substituted by 1, 2 or 3 $R_f$;

$R_6$ is selected from H, $C_{1-6}$ alkyl, $C_{1-6}$ alkyl-C(=O)—, $C_{1-6}$ alkyl-S(=O)—, $C_{1-6}$ alkyl-S(=O)$_2$— and $C_{1-6}$ alkyl-O—C(=O)—, wherein the $C_{1-6}$ alkyl, $C_{1-6}$ alkyl-C(=O)—, $C_{1-6}$ alkyl-S(=O)—, $C_{1-6}$ alkyl-S(=O)$_2$— and $C_{1-6}$ alkyl-O—C(=O)— are optionally substituted by $R_g$;

each of $R_a$, $R_b$, $R_c$, $R_d$, $R_e$, $R_f$ and $R_g$ is independently selected from F, Cl, Br, I, OH, NH$_2$ and $C_{1-3}$ alkyl, wherein the $C_{1-3}$ alkyl is optionally substituted by 1, 2 or 3 R;

each R is independently selected from F, Cl, Br, I, OH, NH$_2$;

the 4-7 membered heterocycloalkyl contains 1, 2, 3 or 4 heteroatoms or heteroatomic groups independently selected from —NH—, —O—, —S— and N;

the carbon atom labeled with "*" is a chiral carbon atom, and exists in the form of (R) or (S) single enantiomer or enriched in one enantiomer.

In some embodiments of the present disclosure, each of $R_a$, $R_b$, $R_c$, $R_d$, $R_e$ and $R_f$ is independently selected from F, Cl, Br, I, OH and NH$_2$, the other variants are as defined in the present disclosure.

In some embodiments of the present disclosure, $R_1$ is selected from H, F, Cl, Br, I, OH, NH$_2$ and CH$_3$, the other variants are as defined in the present disclosure.

In some embodiments of the present disclosure, $R_2$ is selected from H, F, Cl, Br, I, OH, NH$_2$, CH$_3$ and Et, the other variants are as defined in the present disclosure.

In some embodiments of the present disclosure, $R_3$ is selected from H, F, Cl, Br, I, CH$_3$ and Et, the other variants are as defined in the present disclosure.

In some embodiments of the present disclosure, $R_2$ and $R_3$ are attached together to form a ring, the ring is selected from $C_{3-6}$ cycloalkyl and 5-6 membered heterocycloalkyl, the $C_{3-6}$ cycloalkyl and 5-6 membered heterocycloalkyl are optionally substituted by 1, 2 or 3 $R_d$, $R_d$ and the other variants are as defined in the present disclosure.

In some embodiments of the present disclosure, $R_2$ and $R_3$ are attached together to form a ring, the ring is selected from cyclopropyl, cyclobutyl, cyclopentyl, cyclohexyl, tetrahydrofuranyl, tetrahydropyranyl and piperidinyl, wherein the cyclopropyl, cyclobutyl, cyclopentyl, cyclohexyl, tetrahydrofuranyl, tetrahydropyranyl and piperidinyl are optionally substituted by 1, 2 or 3 $R_d$, $R_d$ and the other variants are as defined in the present disclosure.

In some embodiments of the present disclosure, $R_2$ and $R_3$ are attached together to form a ring, the ring is selected from the other variants are as defined in the present disclosure.

In some embodiments of the present disclosure, $R_4$ is selected from OH and NH$_2$, the other variants are as defined in the present disclosure.

In some embodiments of the present disclosure, each of $R_{51}$, $R_{52}$, $R_{53}$, $R_{54}$ and $R_{55}$ is independently selected from H, F, Cl, Br, I, OH, NH$_2$, $C_{1-3}$ alkyl, $C_{1-3}$ alkylamino and $C_{1-3}$ alkoxy, wherein the $C_{1-3}$ alkyl, $C_{1-3}$ alkylamino and $C_{1-3}$ alkoxy are optionally substituted by 1, 2 or 3 $R_f$, $R_f$ and the other variants are as defined in the present disclosure.

In some embodiments of the present disclosure, each of $R_{51}$, $R_{52}$, $R_{53}$, $R_{54}$ and $R_{55}$ is independently selected from H, F, Cl, Br, I, OH, NH$_2$, CH$_3$, Et and the other variants are as defined in the present disclosure.

In some embodiments of the present disclosure, $R_6$ is selected from H, $C_{1-3}$ alkyl, $C_{1-3}$ alkyl-C(=O)—, $C_{1-3}$ alkyl-S(=O)—, $C_{1-3}$ alkyl-S(=O)$_2$— and $C_{1-4}$ alkyl-O—C(=O)—, wherein the $C_{1-3}$ alkyl, $C_{1-3}$ alkyl-C(=O)—, $C_{1-3}$ alkyl-S(=O)—, $C_{1-3}$ alkyl-S(=O)$_2$— and $C_{1-4}$ alkyl-O—C(=O)— are optionally substituted by $R_g$, $R_g$ and the other variants are as defined in the present disclosure.

In some embodiments of the present disclosure, $R_6$ is selected from H, CH$_3$, CH$_3$—C(=O)—, CH$_3$—S(=O)$_2$—, CH$_3$—O—C(=O)— and the other variants are as defined in the present disclosure.

The present disclosure also provides a compound represented by formula (I), an isomer thereof or a pharmaceutically acceptable salt thereof, (I)

wherein, $R_1$ is selected from H, F, Cl, Br, I, OH, NH$_2$ and $C_{1-3}$ alkyl, wherein the $C_{1-3}$ alkyl is optionally substituted by 1, 2 or 3 $R_a$;

$R_2$ is selected from H, F, Cl, Br, I, OH, NH$_2$ and $C_{1-6}$ alkyl, wherein the $C_{1-6}$ alkyl is optionally substituted by 1, 2 or 3 $R_b$;

$R_3$ is selected from H, F, Cl, Br, I and $C_{1-6}$ alkyl, wherein the $C_{1-6}$ alkyl is optionally substituted by 1, 2 or 3 $R_e$;

or, $R_2$ and $R_3$ are attached together to form a ring, the ring is selected from $C_{3-7}$ cycloalkyl and 4-7 membered heterocycloalkyl, the $C_{3-7}$ alkyl and 4-7 membered heterocycloalkyl are optionally substituted by 1, 2 or 3 $R_d$;

$R_4$ is selected from OH, NH$_2$, $C_{1-3}$ alkyl and $C_{1-3}$ alkylamino, wherein the $C_{1-3}$ alkyl and $C_{1-3}$ alkylamino are optionally substituted by 1, 2 or 3 $R_e$;

each of $R_{51}$, $R_{52}$, $R_{53}$, $R_{54}$ and $R_{55}$ is independently selected from H, F, Cl, Br, I, OH, $NH_2$, $C_{1-6}$ alkyl, $C_{1-6}$ alkylamino and $C_{1-6}$ alkoxy, wherein the $C_{1-6}$ alkyl, $C_{1-6}$ alkylamino and $C_{1-6}$ alkoxy are optionally substituted by 1, 2 or 3 $R_f$;

each of $R_a$, $R_b$, $R_c$, $R_d$, $R_e$ and $R_f$ is independently selected from F, Cl, Br, I, OH, $NH_2$ and $C_{1-3}$ alkyl, wherein the $C_{1-3}$ alkyl is optionally substituted by 1, 2 or 3 R;

each R is independently selected from F, Cl, Br, I, OH, $NH_2$;

the 4-7 membered heterocycloalkyl contains 1, 2, 3 or 4 heteroatoms or heteroatomic groups independently selected from —NH—, —O—, —S— and N;

the carbon atom labeled with "*" is a chiral carbon atom, and exists in the form of (R) or (S) single enantiomer or enriched in one enantiomer.

In some embodiments of the present disclosure, each of $R_a$, $R_b$, $R_c$, $R_d$, $R_e$ and $R_f$ is independently selected from F, Cl, Br, I, OH, $NH_2$, the other variants are as defined in the present disclosure.

In some embodiments of the present disclosure, $R_1$ is selected from H, F, Cl, Br, I, OH, $NH_2$ and $CH_3$, the other variants are as defined in the present disclosure.

In some embodiments of the present disclosure, $R_2$ is selected from H, F, Cl, Br, I, OH, $NH_2$, $CH_3$ and Et, the other variants are as defined in the present disclosure.

In some embodiments of the present disclosure, $R_3$ is selected from H, F, Cl, Br, I, $CH_3$ and Et, the other variants are as defined in the present disclosure.

In some embodiments of the present disclosure, $R_2$ and $R_3$ are attached together to form a ring, the ring is selected from $C_{3-6}$ cycloalkyl and 5-6 membered heterocycloalkyl, the $C_{3-6}$ cycloalkyl and 5-6 membered heterocycloalkyl are optionally substituted by 1, 2 or 3 $R_d$, the other variants are as defined in the present disclosure.

In some embodiments of the present disclosure, $R_2$ and $R_3$ are attached together to form a ring, the ring is selected from cyclopropyl, cyclobutyl, cyclopentyl, cyclohexyl, tetrahydrofuranyl, tetrahydropyranyl and piperidinyl, wherein the cyclopropyl, cyclobutyl, cyclopentyl, cyclohexyl, tetrahydrofuranyl, tetrahydropyranyl and piperidinyl are optionally substituted by 1, 2 or 3 $R_d$, the other variants are as defined in the present disclosure.

In some embodiments of the present disclosure, $R_2$ and $R_3$ are attached together to form a ring, the ring is selected from the other variants are as defined in the present disclosure.

In some embodiments of the present disclosure, $R_4$ is selected from OH and $NH_2$, the other variants are as defined in the present disclosure.

In some embodiments of the present disclosure, each of $R_{51}$, $R_{52}$, $R_{53}$, $R_{54}$ and $R_{55}$ is independently selected from H, F, Cl, Br, I, OH, $NH_2$, $C_{1-3}$ alkyl, $C_{1-3}$ alkylamino and $C_{1-3}$ alkoxy, wherein the $C_{1-3}$ alkyl, $C_{1-3}$ alkylamino and $C_{1-3}$ alkoxy are optionally substituted by 1, 2 or 3 $R_f$, the other variants are as defined in the present disclosure.

In some embodiments of the present disclosure, each of $R_{51}$, $R_{52}$, $R_{53}$, $R_{54}$ and $R_{55}$ is independently selected from H, F, Cl, Br, I, OH, $NH_2$, $CH_3$, Et and the other variants are as defined in the present disclosure.

Some embodiments of the present disclosure are obtained by arbitrary combinations of the above variables.

In some embodiments of the present disclosure, the compound, the isomer thereof, or the pharmaceutically acceptable salt thereof, which is selected from (I)

(II-1)

wherein, $R_1$, $R_4$, $R_{51}$, $R_{52}$, $R_{53}$, $R_{54}$, $R_{55}$ and $R_6$ are as defined in the present disclosure;

the carbon atom labeled with "*" is a chiral carbon atom, and exists in the form of (R) or (S) single enantiomer or enriched in one enantiomer.

In some embodiments of the present disclosure, the compound, the isomer thereof, or the pharmaceutically acceptable salt thereof, which is selected from

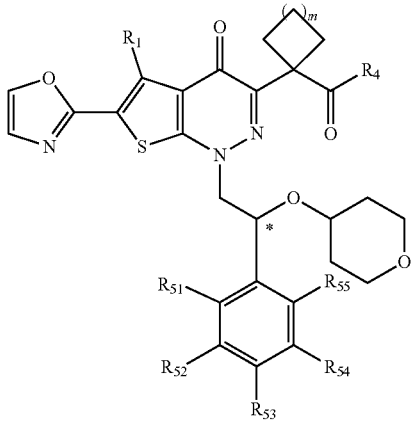

(I-1)

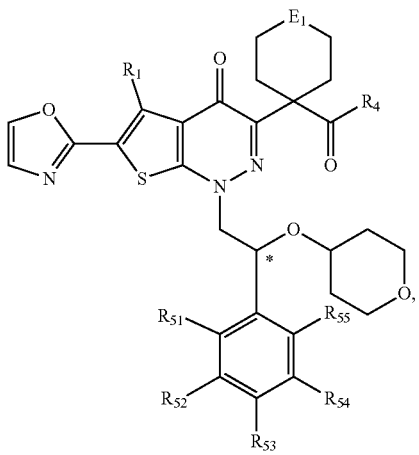

(I-2)

wherein,
m is 0, 1, 2 or 3;
E₁ is —O— or —NH—;
R₁, R₄, R₅₁, R₅₂, R₅₃, R₅₄ and R₅₅ are as defined in the present disclosure;
the carbon atom labeled with "*" is a chiral carbon atom, and exists in the form of (R) or (S) single enantiomer or enriched in one enantiomer.

In some embodiments of the present disclosure, the compound, the isomer thereof, or the pharmaceutically acceptable salt thereof, the compound is selected from

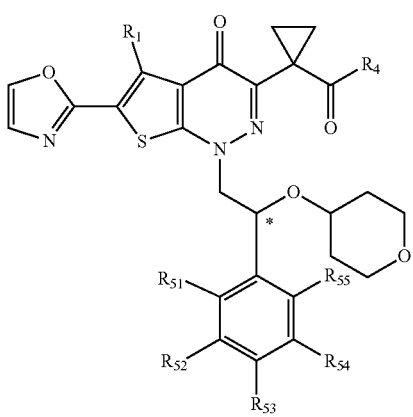

(I-1A)

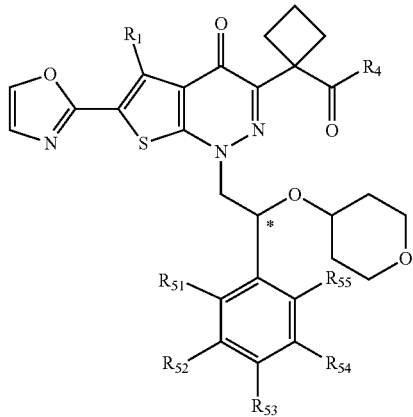

(I-1B)

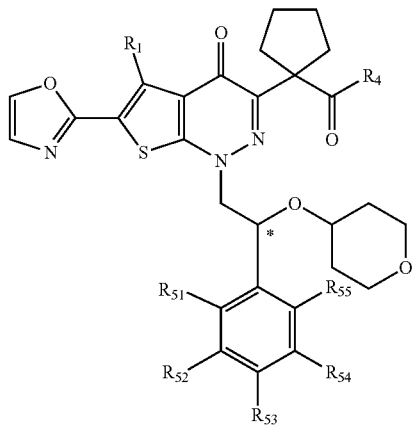

(I-1C)

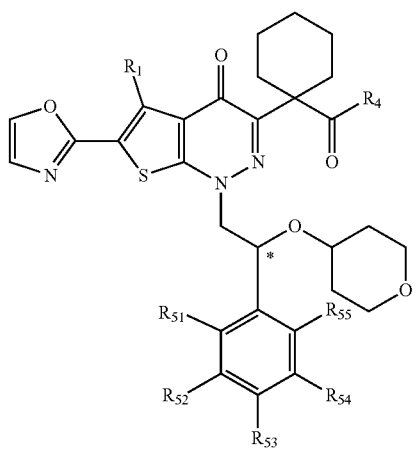

(I-1D)

wherein,
R₁, R₄, R₅₁, R₅₂, R₅₃, R₅₄ and R₅₅ are as defined in the present disclosure;
the carbon atom labeled with "*" is a chiral carbon atom, and exists in the form of (R) or (S) single enantiomer or enriched in one enantiomer.

The present disclosure also provides a compound represented by the following formula, an isomer thereof or a pharmaceutically acceptable salt thereof,

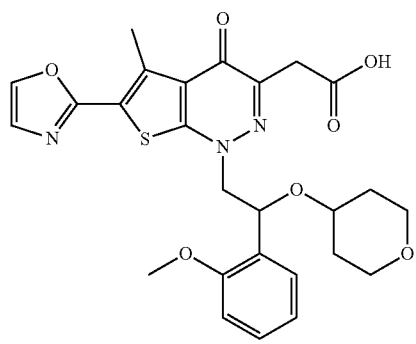
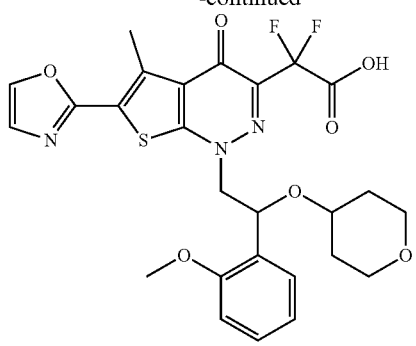
-continued
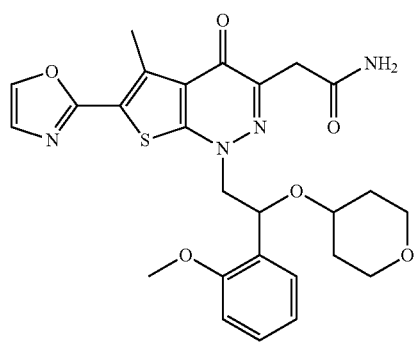
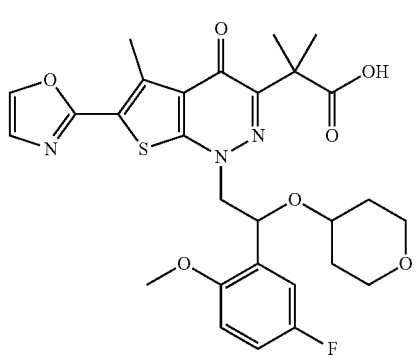
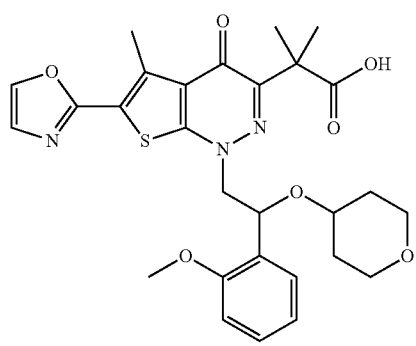
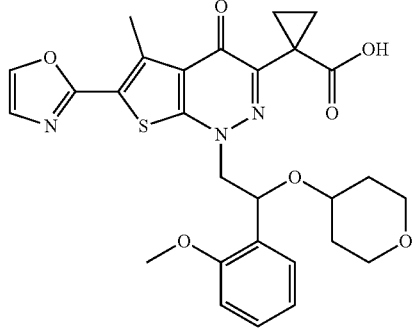
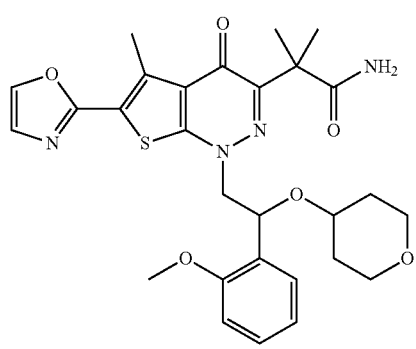
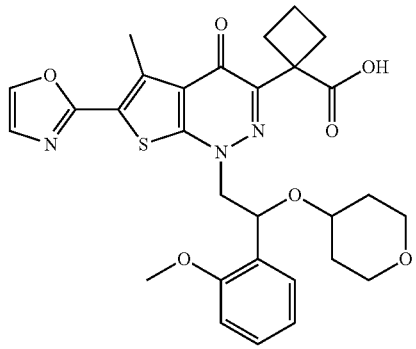

| 11 -continued | 12 -continued |
|---|---|
| 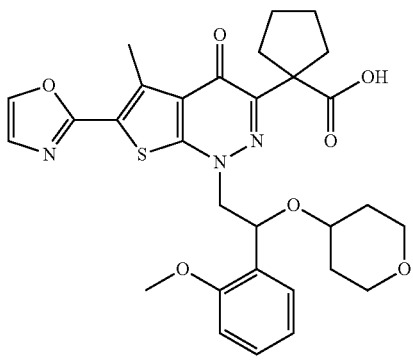 | 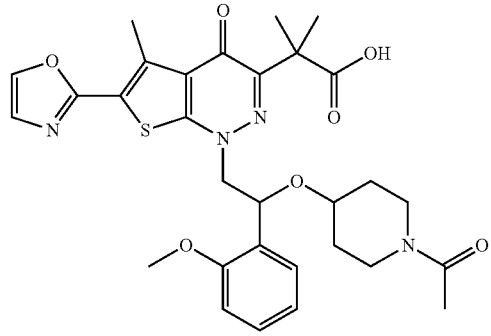 |
| 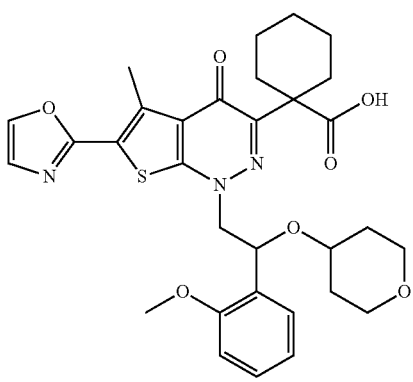 | 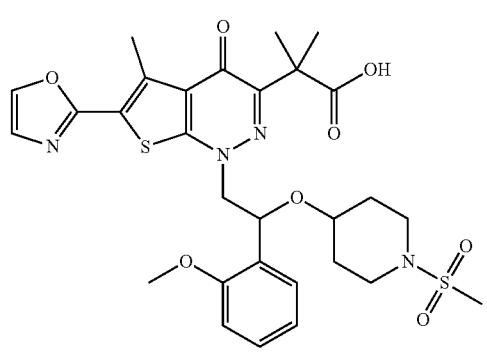 |
| 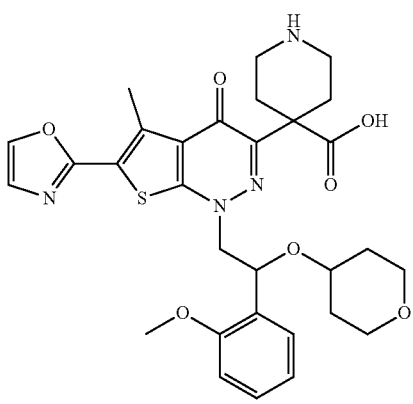 | 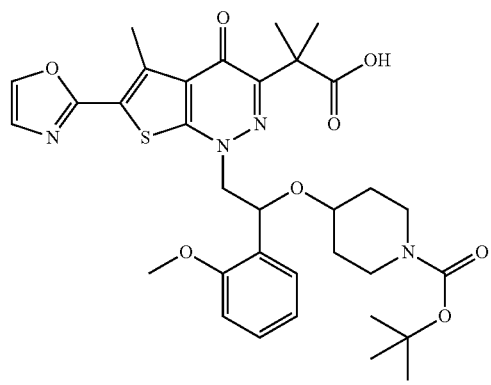 |

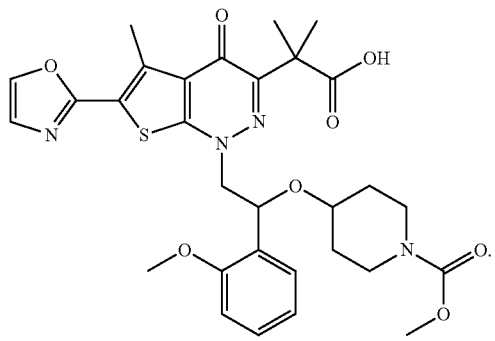
In some embodiments of the present disclosure, the compound, the isomer thereof, or the pharmaceutically acceptable salt thereof,
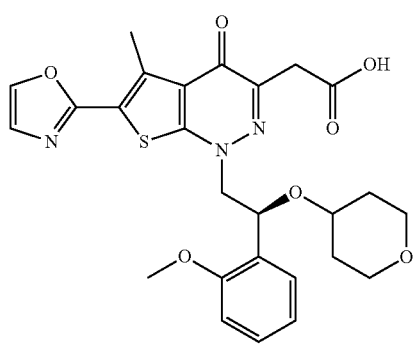
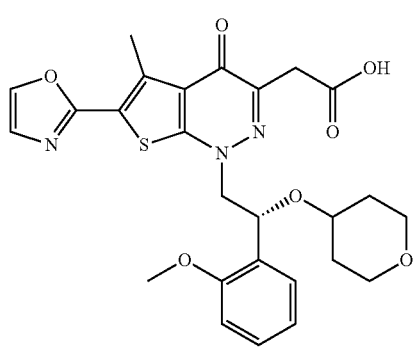
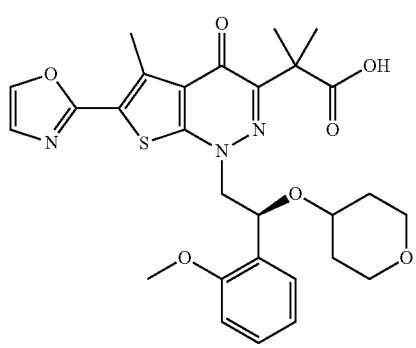
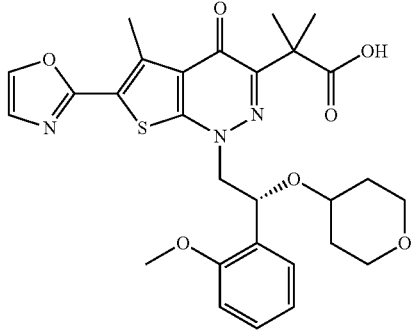
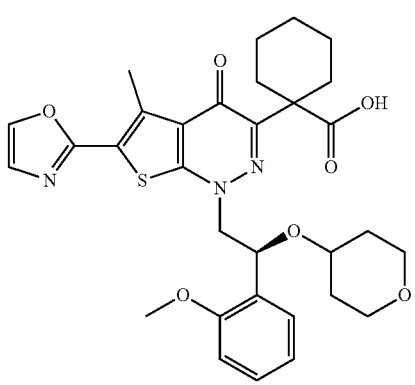
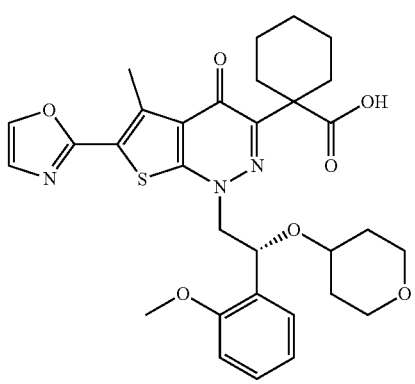
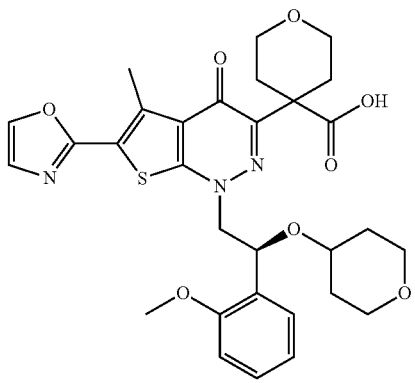

-continued

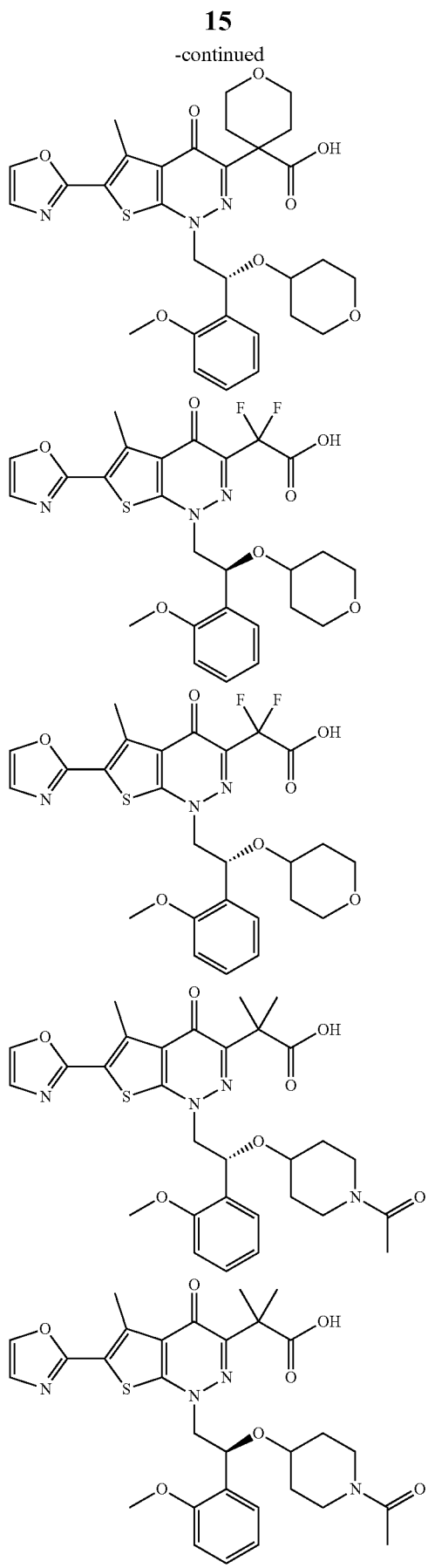

-continued

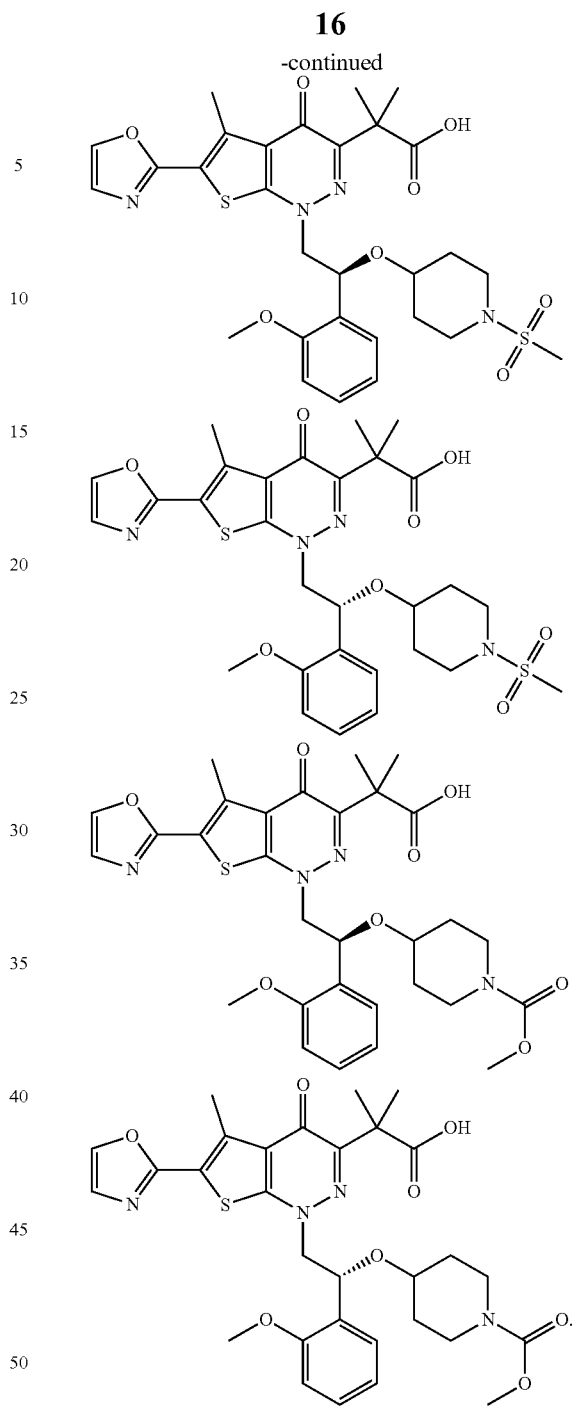

The present disclosure also provides a use of the compound, the isomer thereof or the pharmaceutically acceptable salt thereof in the manufacture of a medicament as ACC1 and ACC2 inhibitor.

Technical Effect

As a new type of ACC1 and ACC2 inhibitor, the compounds of the present disclosure have strong inhibitory activity on human ACC1/ACC2 enzyme; compared with the control compound I-181, the plasma exposure is greatly improved; meanwhile, the compounds of the present disclosure have very good anti-NASH and anti-fibrosis effect.

Definition and Description

Unless otherwise specified, the following terms and phrases when used herein have the following meanings. A specific term or phrase should not be considered indefinite or unclear in the absence of a particular definition, but should be understood in the ordinary sense. When a trading name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and a salt of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(D)" or "(+)" refers to dextrorotation, "(L)" or "(−)" refers to levorotation, and "(DL)" or "(±)" refers to racemic.

Unless otherwise specified, the absolute configuration of a stereogenic center is represented by a wedged solid bond (🖊) and a wedged dashed bond (⸱⸱⸱), and the relative configuration of a stereogenic center is represented by a straight solid bond (🖊) and a straight dashed bond (⸱⸱⸱), a wave line (∿) is used to represent a wedged dashed bond (🖊) or a wedged dashed bond (⸱⸱⸱), or the wave line (∿) is used to represent a straight solid bond (🖊) and a straight dashed bond (⸱⸱⸱). Unless otherwise specified, when double bond structure, such as carbon-carbon double bond, carbon-nitrogen double bond, and nitrogen-nitrogen double bond, exists in the compound, and each of the atom on the double bond is connected to two different substituents (including the condition where a double bond contains a nitrogen atom, the lone pair of electrons attached on the nitrogen atom is regarded as a sub substituent connected), if the atom on the double bond in the compound is connected to its sub substituent by a wave line (∿) this refers to the (Z) isomer, (F) isomer or a mixture of two isomers of the compound. For example, the following formula (A) means that the compound exists as a single isomer of formula (A-1) or formula (A-2) or as a mixture of two isomers of formula (A-1) and formula (A-2); the following formula (B) means that the compound exists in the form of a single isomer of formula (B-1) or formula (B-2) or in the form of a mixture of two isomers of formula (B-1) and formula (B-2). The following formula (C) means that the compound exists as a single isomer of formula (C-1) or formula (C-2) or as two a mixture of two isomers of formula (C-1) and formula (C-2).

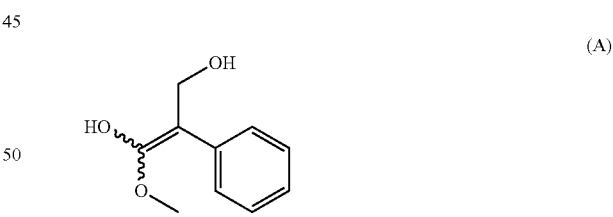

(A)

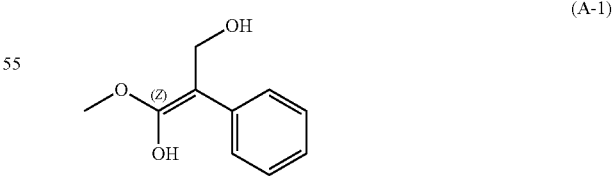

(A-1)

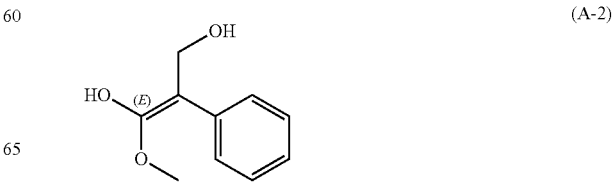

(A-2)

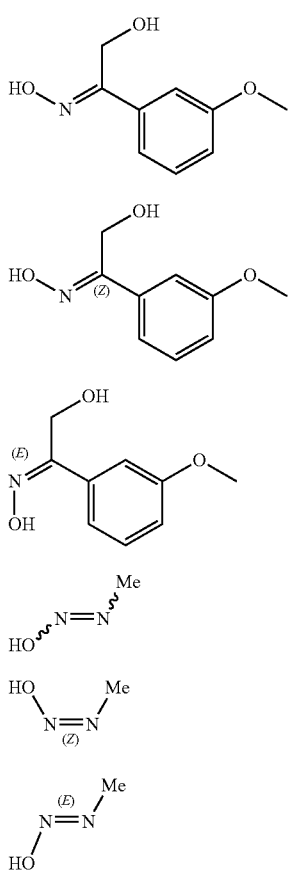

(B)

(B-1)

(B-2)

(C)

(C-1)

(C-2)

Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. Besides, the enantiomer and the diastereoisomer are generally isolated through chromatography which uses a chiral stationary phase and optionally combines with a chemical derivative method (such as carbamate generated from amine). The compound of the present disclosure may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more hydrogen atom(s) on a specific atom are substituted with the substituent, including deuterium and hydrogen variants, as long as the valence of the specific atom is normal and the substituted compound is stable. When the substituent is oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

Unless otherwise specified, the term "hetero" refers to heteroatom or heteroatomic group (i.e., atomic group containing heteroatom), including atoms other than carbon (C) and hydrogen (H) and the atomic groups containing these heteroatoms, for example including oxygen (O), nitrogen (N), sulfur (S), silicon (Si), germanium (Ge), aluminum (Al), boron (B), —O—, —S—, C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, the term "alkyl" refers to linear or branched saturated hydrocarbon groups, in some embodiments, the alkyl is $C_{1-12}$ alkyl; in other embodiments, the alkyl is $C_{1-6}$ alkyl; in other embodiments, the alkyl is $C_{1-3}$ alkyl. It can be monovalent (such as methyl), divalent (such as methylene) or multivalent (such as methine). Examples of alkyl include but are not limited to methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, etc.

Unless otherwise specified, the term "alkoxy" refers to those alkyl groups that are attached to the rest of the molecule through an oxygen atom. Unless otherwise specified, $C_{1-6}$ alkoxy includes $C_1$, $C_2$, $C_3$, $C_4$, $C_5$ and $C_6$ alkoxy. In some embodiments, the alkoxy is $C_{1-3}$ alkoxy. Examples of alkoxy include, but are not limited to: methoxy, ethoxy, n-propoxy, isopropoxy, n-butoxy, sec-butoxy, tert-butoxy, n-pentoxy and S-pentoxy.

Unless otherwise specified, "cycloalkyl" includes any stable cyclic alkyl, including monocyclic, bicyclic or tricyclic ring systems, wherein the bicyclic and tricyclic ring systems include spirocyclic rings, fused rings and bridged rings. In some embodiments, the cycloalkyl is $C_{3-8}$ cycloalkyl; in some embodiments, the cycloalkyl is $C_{3-7}$ cycloalkyl; in other embodiments, the cycloalkyl is $C_{3-6}$ cycloalkyl; in other embodiments, the cycloalkyl is $C_{5-6}$ cycloalkyl. It can be monovalent, divalent or multivalent. Examples of cycloalkyl include, but are not limited to, cyclopropyl, cyclobutyl, cyclopentyl, cyclohexyl, cycloheptyl, norbornyl alkyl, [2.2.2]dicyclooctane, [4.4.0]dicyclodecane, etc.

Unless otherwise specified, the term "heterocycloalkyl" by itself or in combination with other terms means cyclized "heteroalkyl", which includes monocyclic, bicyclic and tricyclic ring systems, wherein bicyclic and tricyclic ring systems include spirocyclic rings, fused rings and bridged ring. Besides, as far as the "heterocycloalkyl" is concerned, a heteroatom may occupy the position of connection between the heterocycloalkyl and the rest of the molecule. In some embodiments, the heterocycloalkyl is 4-7 membered heterocycloalkyl; in some embodiments, the heterocycloalkyl is 4-6 membered heterocycloalkyl; in other embodiments, the heterocycloalkyl is 5-6 membered heterocycloalkyl. Examples of heterocycloalkyl include, but are not limited to, azacyclobutyl, oxacyclobutyl, thiacyclobutyl, pyrrolidyl, pyrazolidinyl, imidazolidinyl, tetrahydrothienyl (including tetrahydrothiophen-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl or oxepanyl.

The compound of the present disclosure can be prepared by a variety of synthetic methods well known to people skilled in the art, including the specific embodiments listed below, embodiments formed by its combination with other chemical synthesis methods and equivalent replacing methods well known to people skilled in the art, preferred implementation method includes but not limited to the embodiments of the present disclosure.

The solvents used in the present disclosure are commercially available. The present disclosure adopts the following abbreviations: aq refers to water; HATU refers to O-(7-azabenzotriazol-1-yl)-N,N,N',N'-tetramethyluronium hexafluorophosphate; eq refers to equivalent, equivalent; DCM refers to dichloromethane; PE refers to petroleum ether; DIAD refers to diisopropyl azodicarboxylate; DMF refers to N,N-dimethylformamide; DMSO refers to dimethyl sulfoxide; EtOAc refers to ethyl acetate; EtOH refers to ethanol; MeOH refers to methanol; BOC refers to tert-butoxycarbonyl, which is an amine protecting group; HOAc refers to acetic acid; r.t. refers to room temperature; THF refers to tetrahydrofuran; Boc$_2$O refers to di-tert-butyl dicarbonate; TFA refers to trifluoroacetic acid; mp refers to melting point; CHLOROFORM-d refers to deuterated chloroform; DMAP refers to dimethylaminopyridine; EDTA-K$_2$ refers to dipotassium ethylenediaminetetraacetate; PEG400 refers to polyethylene glycol 400; DBU refers to 1,8-diazabicyclo[5.4.0]undec-7-ene; NaBH$_4$ refers to sodium borohydride; NBS refers to N-bromosuccinimide; LiHMDS refers to lithium hexamethyldisilazide; BPO refers to dibenzoyl peroxide; SEM-Cl refers to 2-(trimethylsilyl)ethoxymethyl chloride; MSCl refers to methylsulfonyl chloride; TBAF refers to tetrabutylammonium fluoride.

Compounds are named manually or by ChemDraw® software, and commercially available compounds use the supplier catalog name.

DETAILED DESCRIPTION OF THE EMBODIMENT

The following embodiments further illustrate the present disclosure, but they are not setting any limit to the present disclosure in any sense. The present disclosure has been described in detail in the text, and its specific embodiments have also been disclosed, for one skilled person in the art, it is obvious to modify and improve the embodiments of the present disclosure without departing the spirit and scope of the present disclosure.

Reference Example 1: Fragment BB-1

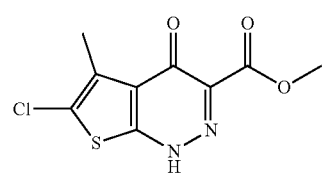

BB-1

Synthetic Route

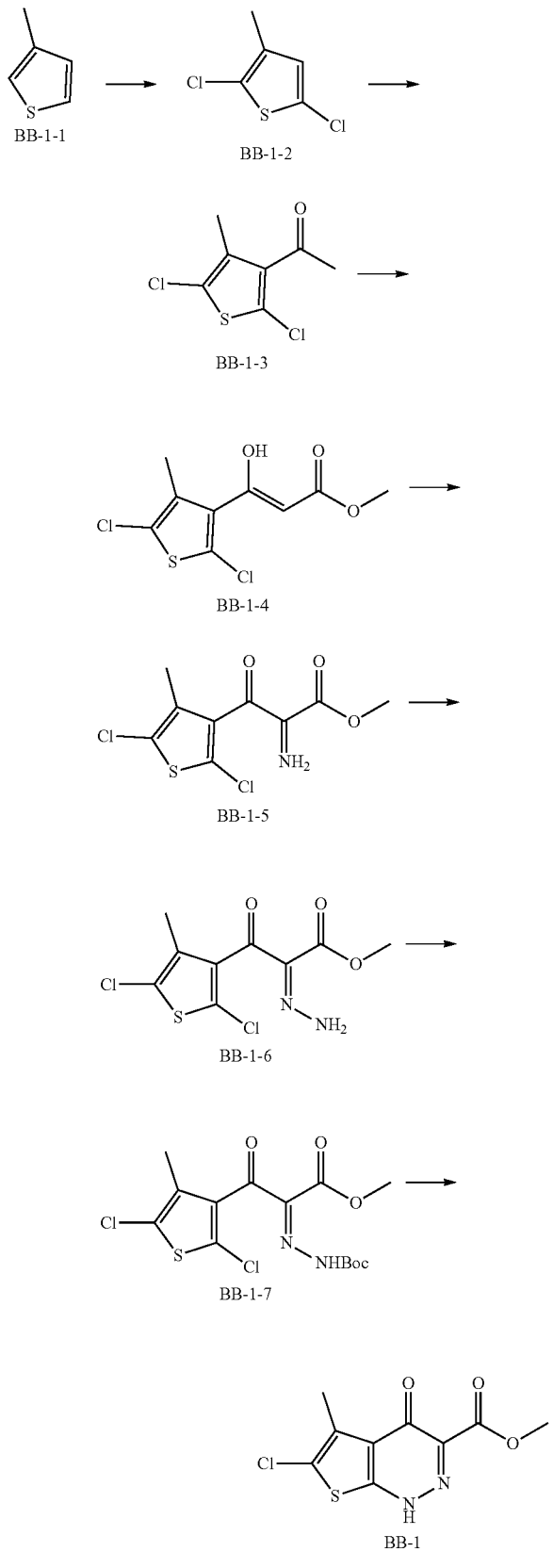

Step 1: Synthesis of Compound BB-1-2

Compound BB-1-1 (25 g, 254.67 mmol) was dissolved in DCM (60 mL), a solution of sulfonyl chloride (43 mL, 430.10 mmol) in DCM (10 mL) was added dropwise at 0° C., and the mixture was stirred overnight at room temperature. After the completion of the reaction, the solvent was removed under reduced pressure to give the crude BB-1-2, which was directly used in the next step. $^1$H NMR (400 MHz, CDCl$_3$) δ 6.62 (s, 1H), 2.14 (s, 3H).

Step 2: Synthesis of Compound BB-1-3

Compound BB-1-2 (40.1 g, 240.04 mmol) was dissolved in chloroform (300 mL), acetyl chloride (34.3 mL, 480.65 mmol) and aluminum trichloride (38.4 g, 287.98 mmol) were added thereto at 0° C., and the mixture was stirred overnight at room temperature. After the completion of the reaction, the reaction mixture was poured into ice water (1000 mL), stirred at room temperature for 30 minutes, and extracted with EtOAc (500 mL×2). The combined organic phase was washed with saturated brine (500 mL), dried over anhydrous sodium sulfate, and filtered. The solvent was removed under reduced pressure, and the residue was purified by column chromatography to give BB-1-3. $^1$H NMR (400 MHz, CDCl$_3$) δ 2.64 (s, 3H), 2.26 (s, 3H).

Step 3: Synthesis of Compound BB-1-4

Under nitrogen atmosphere, sodium hydride (12.7 g, 60% dispersed in mineral oil, 317.53 mmol) was added to toluene (200 mL), dimethyl carbonate (17.9 mL, 212.63 mmol) was added thereto, and the temperature was raised to 120° C. A solution of compound BB-1-3 (22.2 g, 106.17 mmol) in toluene (50 mL) was added dropwise over half an hour, and the reaction was allowed to continue for another half an hour. After the completion of the reaction, the mixture was quenched with water (300 mL) and the aqueous phase was extracted with EtOAc (150 mL×2). The combined organic phase was washed with saturated brine (100 mL×2), dried over anhydrous sodium sulfate, filtered, and the solvent was removed under reduced pressure. The residue was purified by column chromatography to give BB-1-4. $^1$H NMR (400 MHz, CDCl$_3$) δ 12.13 (s, 1H), 5.28 (s, 1H), 3.78 (s, 3H), 2.10 (s, 3H).

Step 4: Synthesis of Compound BB-1-5

Compound BB-1-4 (4.7 g, 17.59 mmol) and triethylamine (2.9 mL, 20.84 mmol) were added to acetonitrile (50 mL), p-toluenesulfonyl azide (4.2 g, 21.30 mmol) was added thereto at 0° C., and the reaction was allowed to continue at this temperature for 30 minutes, and then at room temperature for 2 hours. After the completion of the reaction, the mixture was quenched with water (50 mL) at 0° C., and the aqueous phase was extracted with EtOAc (25 mL×2). The combined organic phase was washed with saturated brine (10 mL×2), dried over anhydrous sodium sulfate, filtered, and the solvent was removed under reduced pressure. The residue was purified by column chromatography to give BB-1-5. $^1$H NMR (400 MHz, CDCl$_3$) δ 3.83 (s, 3H), 2.12 (s, 3H).

Step 5: Synthesis of Compound BB-1-6

Compound BB-1-5 (22.6 g, 77.10 mmol) was added to isopropyl ether (300 mL), a solution of tributylphosphine (20.9 mL, 84.71 mmol) in n-hexane (30 mL) was added dropwise at 0° C., and the mixture was stirred at room temperature for 2 hours. After the completion of the reaction, the solvent was removed under reduced pressure, and the residue was purified by column chromatography to give BB-1-6. $^1$H NMR (400 MHz, CDCl$_3$) δ 3.92 (s, 3H), 2.12 (s, 3H).

Step 6: Synthesis of Compound BB-1-7

Compound BB-1-6 (20.1 g, 68.10 mmol) was dissolved in DCM (300 mL), Boc₂O (17.8 g, 81.56 mmol) and DMAP (1.7 g, 13.92 mmol) were added thereto, and the mixture was stirred at room temperature for 12 hours. After the completion of the reaction, the solvent was removed under reduced pressure, and the residue was purified by column chromatography to give BB-1-7. ¹H NMR (400 MHz, CDCl₃) δ 3.93 (s, 3H), 2.22 (s, 3H), 1.54 (s, 9H).

Step 7: Synthesis of Compound BB-1

Compound BB-1-7 (26.1 g, 66.03 mmol) was dissolved in DMF (100 mL), K₂CO₃ (10.95 g, 79.24 mmol) was added thereto, and the reaction was allowed to run at 80° C. for 12 hours. After the completion of the reaction, water (300 mL) and HCl (1 M, 100 mL) were added, and the resulting aqueous phase was extracted with EtOAc (300 mL×2). The combined organic phase was dried over anhydrous sodium sulfate, filtered, and the solvent was removed under reduced pressure, the residue was purified by column chromatography to give the target compound. LCMS: [M+H]⁺ 258.8.

Reference Example 2: Fragment BB-2

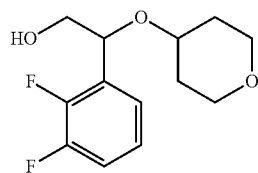

Synthetic Route

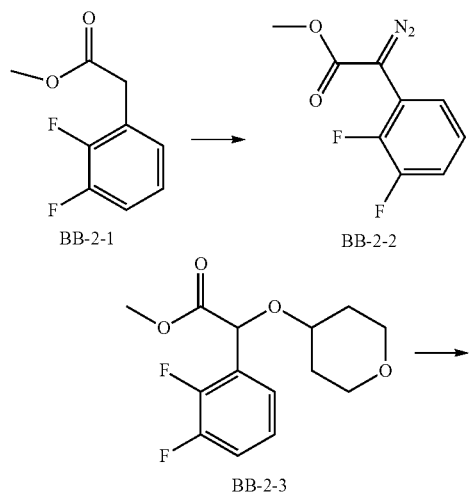

Step 1: Synthesis of Compound BB-2-2

Compound BB-2-1 (4 g, 21.49 mmol) was dissolved in acetonitrile (50 mL), a solution of DBU (4.91 g, 32.23 mmol) and 4-acetamidobenzenesulfonyl azide (6.19 g, 25.78 mmol) in acetonitrile (10 mL) was added, and the resulting mixture was stirred overnight at room temperature. After the completion of the reaction, the solvent was removed by rotary evaporation under reduced pressure, and the residue was separated by column chromatography to give the target compound BB-2-2. ¹H NMR (400 MHz, CDCl₃) δ 7.56-7.53 (m, 1H), 7.23-7.20 (m, 1H), 7.12-7.08 (m, 1H), 3.77 (s, 3H).

Step 2: Synthesis of Compound BB-2-3

Compound BB-2-2 (0.99 g, 4.67 mmol) and 4-tetrahydropyranol (930 μL, 9.29 mmol) were dissolved in DCM (50 mL), rhodium acetate dimer (41 mg, 93 μmol) was added thereto, and the reaction was allowed to run at room temperature for 5 minutes. After the completion of the reaction, the solvent was removed under reduced pressure, and the residue was separated by column chromatography to give BB-2-3. ¹H NMR (400 MHz, CDCl₃) δ 7.49-7.47 (m, 1H), 7.10-7.03 (m, 1H), 6.99-6.91 (m, 1H), 5.39 (s, 1H), 3.94-3.81 (m, 2H), 3.66 (s, 3H), 3.59-3.51 (m, 1H), 3.41-3.28 (m, 2H), 1.96-1.87 (m, 1H), 1.83-1.73 (m, 1H), 1.70-1.55 (m, 2H).

Step 3: Synthesis of Compound BB-2

Compound BB-2-3 (5.2 g, 18.16 mmol) was dissolved in methanol (100 mL), NaBH₄ (687 mg, 18.16 mmol) was added at 0° C., and the reaction was allowed to run at room temperature for 2 hours. After the completion of the reaction, water (50 mL) was added dropwise to quench the reaction at 0° C. The mixture was filtered, and the solvent was removed under reduced pressure. Water (50 mL) was added to the residue and then extracted with DCM (50 mL×2). The combined organic phase was washed with saturated brine (50 mL), dried over anhydrous sodium sulfate, filtered, and dried by rotary evaporation, and the resulting residue was separated by column chromatography to give the target compound BB-2. ¹H NMR (400 MHz, CDCl₃) δ 7.52-7.49 (m, 1H), 7.14-7.12 (m, 1H), 7.05-7.01 (m, 1H), 5.05-5.01 (m, 1H), 3.99-3.96 (m, 1H), 3.92-3.90 (m, 1H), 3.72-3.70 (m, 1H), 3.57-3.32 (m, 4H), 2.26-2.23 (m, 1H), 2.05-1.96 (m, 1H), 1.79-1.63 (m, 2H), 1.60-1.54 (m, 1H).

Reference Example 3: Fragment BB-3

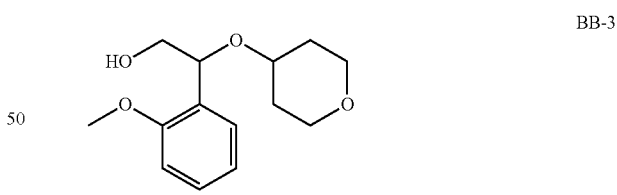

Synthetic route:

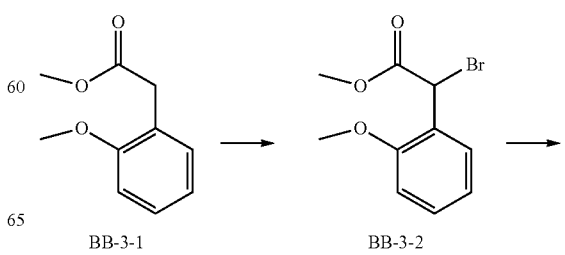

27
-continued

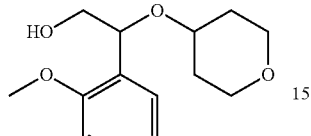

BB-3-3

BB-3

Step 1: Synthesis of Compound BB-3-2

Compound BB-3-1 (50 g, 277.47 mmol) and NBS (49.39 g, 277.47 mmol) were dissolved in carbon tetrachloride (1 L), BPO (1.01 g, 4.16 mmol) was added thereto, and the reaction was allowed to run at 80° C. for 3 hours. After the completion of the reaction, the solvent was removed from the reaction mixture under reduced pressure to give the target compound BB-3-2, which was used directly in the next step. $^1$H NMR (400 MHz, CDCl$_3$) δ 7.64-7.61 (m, 1H), 7.37-7.30 (m, 1H), 7.03-6.98 (m, 1H), 6.91-6.88 (m, 1H), 5.91 (s, 1H), 3.89 (s, 3H), 3.79 (s, 3H).

Step 2: Synthesis of Compound BB-3-3

Compound BB-3-2 (76.1 g, 293.71 mmol) and 4-tetrahydropyranol (58.8 mL, 587.24 mmol) were dissolved in DCM (1.2 L), silver oxide (68.1 g, 293.87 mmol) was added thereto, and the mixture was stirred at 25° C. for 16 hours. After the completion of the reaction, the mixture was filtered and the solvent was removed under reduced pressure. The resulting residue was purified by column chromatography to give the target compound BB-3-3. $^1$H NMR (400 MHz, CDCl$_3$) δ 7.48-7.43 (m, 1H), 7.35-7.31 (m, 1H), 7.02-7.01 (m, 1H), 6.94-6.90 (m, 1H), 5.51 (s, 1H), 4.02-3.92 (m, 2H), 3.87 (s, 3H), 3.73 (s, 3H), 3.65-3.60 (m, 1H), 3.48-3.36 (m, 2H), 2.03-1.94 (m, 1H), 1.92-1.83 (m, 1H), 1.79-1.65 (m, 2H).

Step 3: Synthesis of Compound BB-3

Compound BB-3-3 (42.1 g, 150.19 mmol) was dissolved in methanol (300 mL), NaBH$_4$ (28.4 g, 750.94 mmol) was added in batches at 0° C., and the reaction was allowed to run at room temperature for 2 hours. After the completion of the reaction, water (100 mL) was added dropwise at 0° C. to quench the reaction, and the solvent was removed under reduced pressure. Water (200 mL) was added to the residue and then extracted with DCM (250 mL×2). The combined organic phase was washed with saturated brine (100 mL), dried over anhydrous sodium sulfate, filtered, dried by rotary evaporation, and the resulting residue was separated by column chromatography to give the target compound BB-3. $^1$H NMR (400 MHz, CDCl$_3$) δ 7.48-7.40 (m, 1H), 7.33-7.28 (m, 1H), 7.03-7.00 (m, 1H), 6.94-6.85 (m, 1H), 5.11-5.05 (m, 1H), 4.01-3.90 (m, 2H), 3.84 (s, 3H), 3.70-3.66 (m, 1H), 3.58-3.46 (m, 2H), 3.45-3.33 (m, 2H), 2.38-2.19 (m, 1H), 2.06-1.97 (m, 1H), 1.84-1.75 (m, 1H), 1.72-1.60 (m, 2H).

28
Example 1: WX001

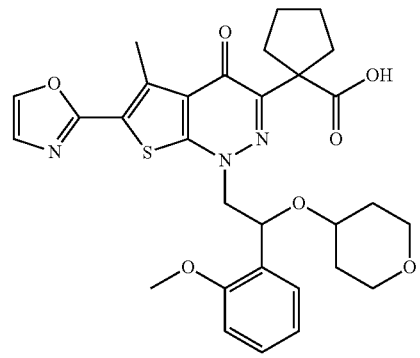

WX-001

Synthetic Route

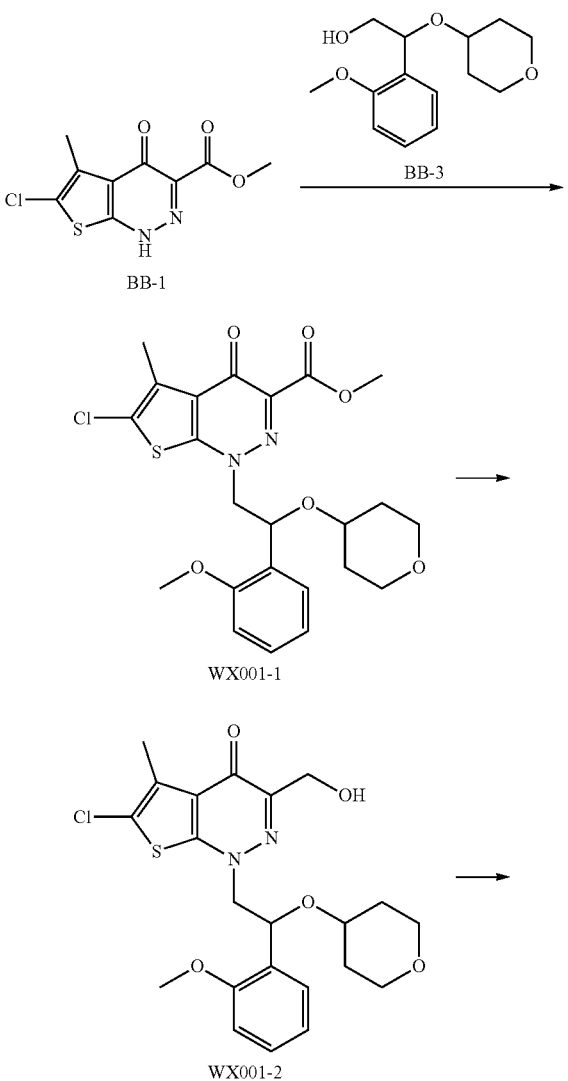

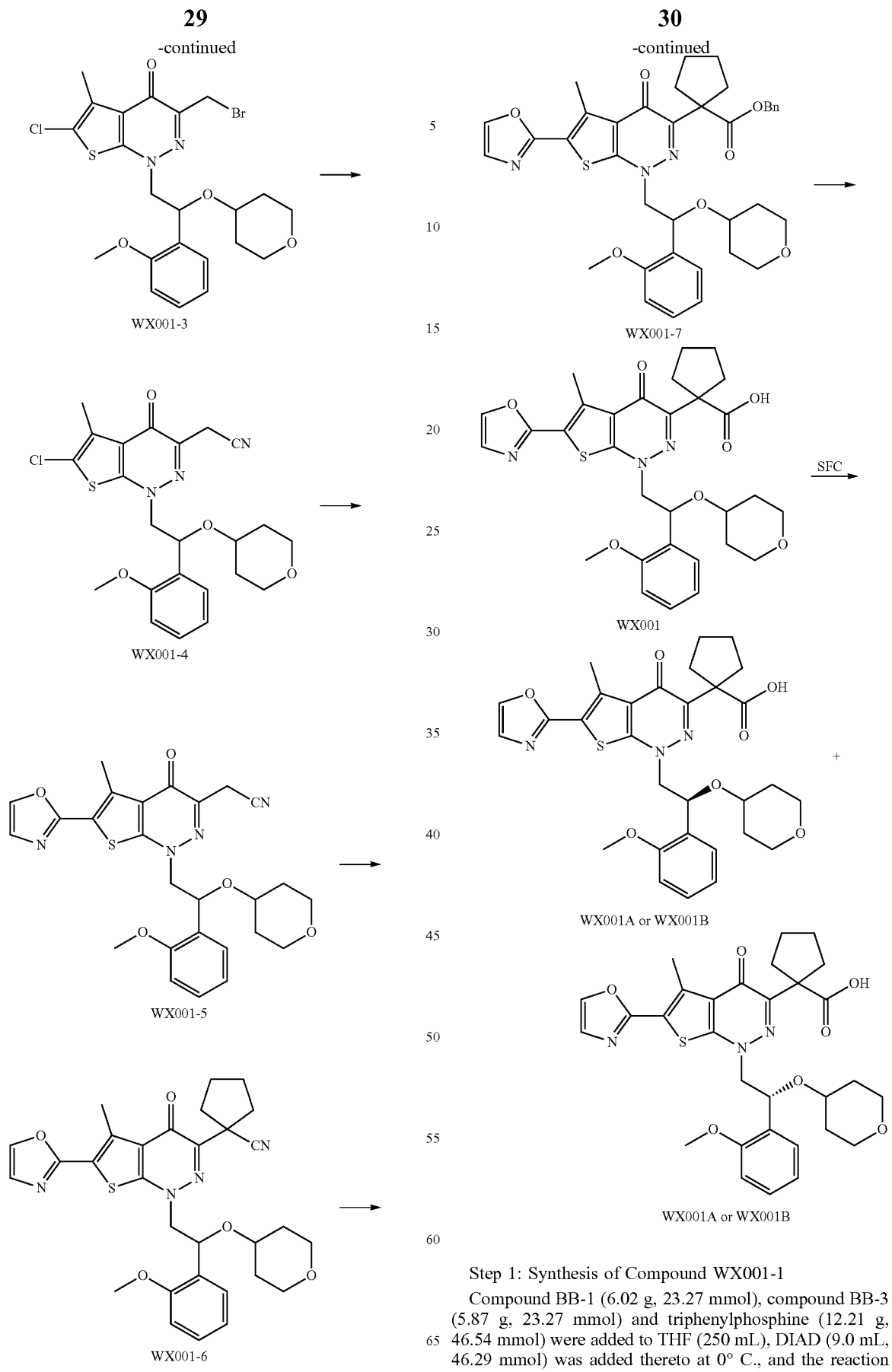
Step 1: Synthesis of Compound WX001-1
Compound BB-1 (6.02 g, 23.27 mmol), compound BB-3 (5.87 g, 23.27 mmol) and triphenylphosphine (12.21 g, 46.54 mmol) were added to THF (250 mL), DIAD (9.0 mL, 46.29 mmol) was added thereto at 0° C., and the reaction was allowed to run at room temperature for 2 hours. After the completion of the reaction, the mixture was filtered, and the solvent was removed under reduced pressure. The residue was separated by chromatography column to give the target compound WX001-1. $^1$H NMR (400 MHz, CDCl$_3$) δ 7.56-7.54 (m, 1H), 7.38-7.34 (m, 1H), 7.08-7.04 (m, 1H), 6.93-6.91 (m, 1H), 5.44-5.41 (m, 1H), 4.43-4.39 (m, 1H), 4.17-4.12 (m, 1H), 4.01 (s, 3H), 3.90 (s, 3H), 3.73-3.65 (m, 1H), 3.59-3.49 (m, 1H), 3.31-3.28 (m, 1H), 3.27-3.20 (m, 2H), 2.62 (s, 3H), 1.78-1.66 (m, 1H), 1.64-1.48 (m, 2H), 1.29-1.23 (m, 1H).

Step 2: Synthesis of Compound WX001-2

NaBH$_4$ (1.73 g, 45.64 mmol) was dissolved in methanol (70 mL), compound WX001-1 (4.5 g, 9.13 mmol) was added in batches at 0° C., and the reaction was allowed to run at 50° C. for 1 hour. The reaction mixture was quenched with water (20 mL) at 0° C., and extracted with DCM (25 mL×2). The organic phase was combined, washed with saturated brine (20 mL), dried over anhydrous sodium sulfate, filtered, and the solvent was removed under reduced pressure. The residue was used directly in the next step.

Step 3: Synthesis of Compound WX001-3

Under nitrogen atmosphere, compound WX001-2 (4.2 g, 9.03 mmol) and phosphorus tribromide (940 μL, 9.90 mmol) were dissolved in DCM (50 mL), and the reaction was allowed to run at room temperature for half an hour. After the completion of the reaction, the solvent was removed under reduced pressure, and the resulting residue was separated by chromatography column to give the target compound WX001-3. $^1$H NMR (400 MHz, CDCl$_3$) δ 7.56-7.54 (m, 1H), 7.37-7.33 (m, 1H), 7.07-7.03 (m, 1H), 6.93-6.91 (m, 1H), 5.43-5.40 (m, 1H), 4.64 (d, J=9.2 Hz, 1H), 4.57 (d, J=9.2 Hz, 1H), 4.38-4.33 (m, 1H), 4.07-4.04 (m, 1H), 3.91 (s, 3H), 3.75-3.65 (m, 1H), 3.63-3.52 (m, 1H), 3.42-3.25 (m, 3H), 2.62 (s, 3H), 1.74-1.64 (m, 1H), 1.59-1.54 (m, 2H), 1.24-1.20 (m, 1H).

Step 4: Synthesis of Compound WX001-4

Compound WX001-3 (3.8 g, 7.20 mmol) was dissolved in DMF (10 mL), KCN (2 g, 30.71 mmol) was added thereto, and the reaction was allowed to run at room temperature for 2 hours. TLC detected that the raw material was still remained, KCN (1.6 g, 24.57 mmol) was added, and the reaction was allowed to continue for another 2.5 hours. After the completion of the reaction, the mixture was quenched with water (50 mL) at 0° C., and extracted with EtOAc (25 mL×2). The organic phase was combined, washed with saturated brine (25 mL), and dried over anhydrous sodium sulfate, filtered, and the solvent was removed under reduced pressure. The resulting residue was separated by chromatography column to give the target compound WX001-4. $^1$H NMR (400 MHz, CDCl$_3$) δ 7.50-7.37 (m, 1H), 7.31-7.22 (m, 1H), 6.98-6.94 (m, 1H), 6.86-6.84 (m, 1H), 5.39-5.36 (m, 1H), 4.41-4.24 (m, 1H), 4.05-3.99 (m, 1H), 3.98-3.75 (m, 5H), 3.74-3.63 (m, 1H), 3.56-3.46 (m, 1H), 3.33-3.29 (m, 1H), 3.28-3.15 (m, 2H), 2.51 (s, 3H), 1.71-1.61 (m, 1H), 1.59-1.41 (m, 2H), 1.16-1.04 (m, 1H).

Step 5: Synthesis of Compound WX001-5

Compound WX001-4 (2.83 g, 5.97 mmol), 2-(tri-n-butylstannyl)oxazole (5.35 g, 14.93 mmol) were dissolved in toluene (100 mL), and tetrakis(triphenylphosphine)palladium (2.07 g, 1.79 mmol) was added thereto. The reaction mixture was purged with nitrogen for 3 times and raised to 120° C., and the reaction was allowed to run for 1 hour. The reaction mixture was reduced to room temperature and the solvent was removed under reduced pressure. The residue was dissolved in DCM (30 mL) and quenched with saturated potassium fluoride (30 mL). The mixture was extracted with DCM (30 mL), the combined organic phase was washed with saturated brine (30 mL), dried over anhydrous sodium sulfate, filtered, and the solvent was removed under reduced pressure. The residue was separated by chromatography column to give the target compound WX001-5. $^1$H NMR (400 MHz, CDCl$_3$) δ 7.71 (s, 1H), 7.48-7.45 (m, 1H), 7.27-7.26 (m, 1H), 7.21 (s, 1H), 6.99-6.95 (m, 1H), 6.86-6.84 (m, 1H), 5.45-5.41 (m, 1H), 4.42-4.38 (m, 1H), 4.14-4.09 (m, 1H), 3.94-3.82 (m, 5H), 3.71-3.62 (m, 1H), 3.54-3.43 (m, 1H), 3.30-3.35 (m, 1H), 3.27-3.12 (m, 2H), 2.95 (s, 3H), 1.70-1.60 (m, 1H), 1.57-1.47 (m, 2H), 1.12-1.09 (m, 1H).

Step 6: Synthesis of Compound WX001-6

Compound WX001-5 (0.1 g, 197.41 μmol) was dissolved in THF (10 mL), LiHMDS (1M, 590 μL, 590 μmol) was added dropwise at −65° C., and the reaction was allowed to run for half an hour. Then 1,4-dibromobutane (70 μL, 580.32 μmol) was added dropwise, and the reaction was allowed to continue at room temperature for half an hour. After the completion of the reaction, water (10 mL) was added dropwise to quench the reaction at 0° C., and extracted with EtOAc (10 mL×2). The organic phase was combined and washed with saturated brine (10 mL), dried over anhydrous sodium sulfate, filtered to remove the desiccant, and the solvent was removed under reduced pressure. The residue was separated by preparation plate to give the target compound WX001-6. LCMS (5-95/1.5 min): 0.973 min, [M+H]$^P$=561.1.

Step 7: Synthesis of Compound WX001-7

Compound WX001-6 (140 mg, 249.70 μmol) was dissolved in benzyl alcohol (1 mL), a solution of hydrogen chloride in 1,4-dioxane (4 M, 62 μL, 248 μmol) was added under nitrogen atmosphere, and the reaction was allowed to run at 50° C. for 2 hours. After the completion of the reaction, the solvent was removed under reduced pressure, and the resulting residue was separated by preparative HPLC to give the target compound WX001-7 (hydrochloric acid condition). LCMS (5-95/1.5 min): 1.095 min, [M+1-1]$^+$=670.1.

Step 8: Synthesis of Compound WX001

Compound WX001-7 (0.14 g, 209.02 μmol) was dissolved in MeOH (10 mL), and 10% Pd/C (30 mg) was added under nitrogen atmosphere. The reaction mixture was purged with hydrogen for 3 times, and the reaction was allowed to run under hydrogen atmosphere (30 Psi) at 30° C. for 2 hours. The reaction mixture was filtered, and the solvent was removed under reduced pressure to give a residue. The residue was separated by preparative chromatography (hydrochloric acid condition) to give the target compound WX001. The compound WX001 was analyzed by supercritical fluid chromatography (column: Chiralpak AD-3 100×4.6 mm I.D., 3 μm; mobile phase: A: supercritical carbon dioxide, B: 0.05% diethylamine in ethanol; gradient: B from 5% to 40% in 4.5 minutes, 40% for 2.5 minutes, back to 5% equilibration for 1 minute; flow rate: 2.8 mL/min; column temperature: 40° C.; wavelength: 220 nm) as racemic compounds. Chiral isomers WX001A and WX001B were separated, and their retention time was 3.954 min and 4.388 min respectively.

Referring to the synthesis method of steps 6-8 in the Embodiment 1, the example in the following table was synthesized using different halide fragments in step 6. The structure in the table also represents its possible isomers.

TABLE 1

Compound structure of each example

| Example | Halide fragment | Structure | Compound |
|---|---|---|---|
| 2 | — | 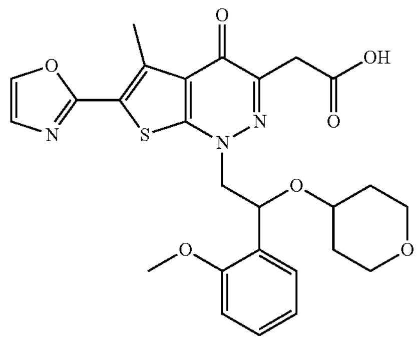 [SMILES: COc1ccccc1C(Cn1nc(CC(=O)O)c(=O)c2c(C)c(-c3ncco3)sc21)OC1CCOCC1] | WX002 |
| | | | WX002A or WX002B |
| | | | WX002B or WX002A |
| 3 | Hydrolyzing the nitrile group in WX001-5 | 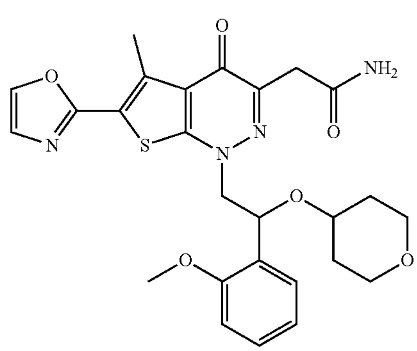 [SMILES: COc1ccccc1C(Cn1nc(CC(N)=O)c(=O)c2c(C)c(-c3ncco3)sc21)OC1CCOCC1] | WX003 |

TABLE 1-continued

Compound structure of each example

| Example | Halide fragment | Structure | Compound |
|---|---|---|---|
| 4 | MeI | 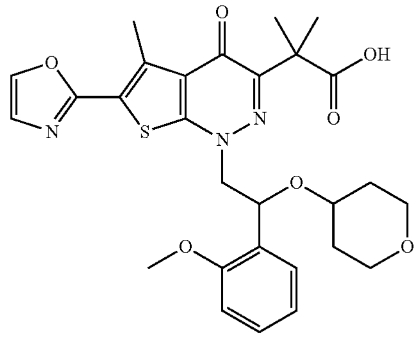 [SMILES: COc1ccccc1C(Cn1nc(C(C)(C)C(=O)O)c(=O)c2c(C)c(-c3ncco3)sc21)OC1CCOCC1] | WX004 |
| | | | WX004A or WX004B |
| | | | WX004B or WX004A |
| 5 | Br–CH₂CH₂–Br | 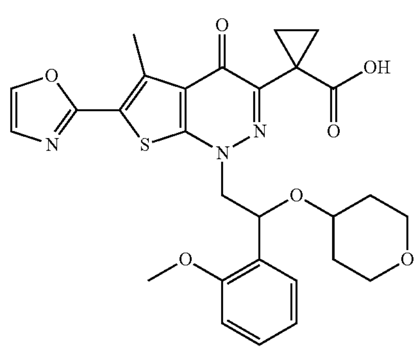 [SMILES: COc1ccccc1C(Cn1nc(C2(C(=O)O)CC2)c(=O)c2c(C)c(-c3ncco3)sc21)OC1CCOCC1] | WX005 |

TABLE 1-continued
Compound structure of each example
| Example | Halide fragment | Structure | Compound |
|---------|----------------|-----------|----------|
| 6 |  | 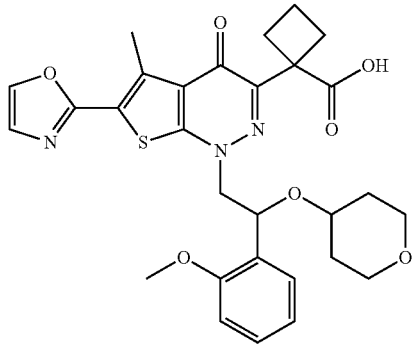 [SMILES: COc1ccccc1C(Cn1nc(C2(C(=O)O)CCC2)c(=O)c2c(C)c(-c3ncco3)sc21)OC1CCOCC1] | WX006 |
| 7 | 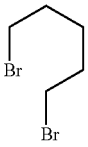 | 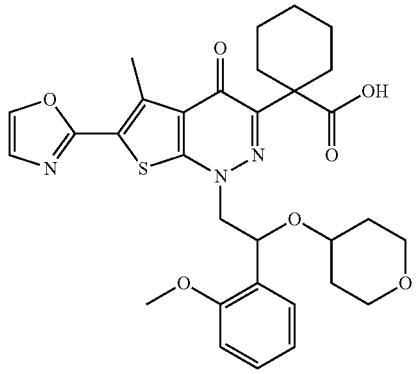 | WX007 |
|   |   | 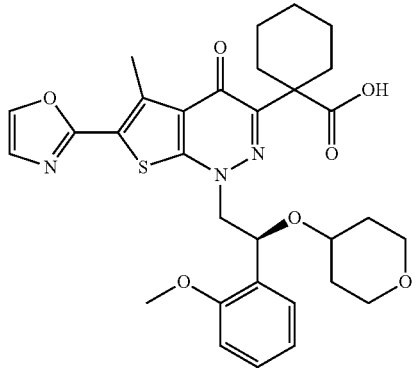 [SMILES: COc1ccccc1[C@@H](Cn1nc(C2(C(=O)O)CCCCC2)c(=O)c2c(C)c(-c3ncco3)sc21)OC1CCOCC1] | WX007A or WX007B |
|   |   | 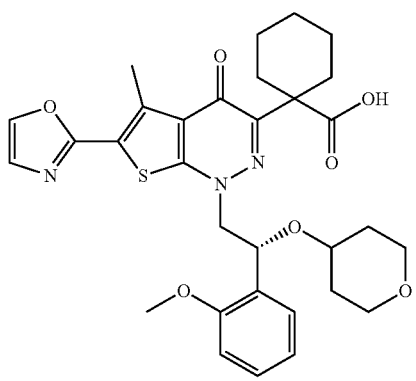 [SMILES: COc1ccccc1[C@H](Cn1nc(C2(C(=O)O)CCCCC2)c(=O)c2c(C)c(-c3ncco3)sc21)OC1CCOCC1] | WX007B or WX007A |

TABLE 1-continued
Compound structure of each example
| Example | Halide fragment | Structure | Compound |
|---|---|---|---|
| 8 | 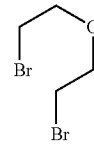 | 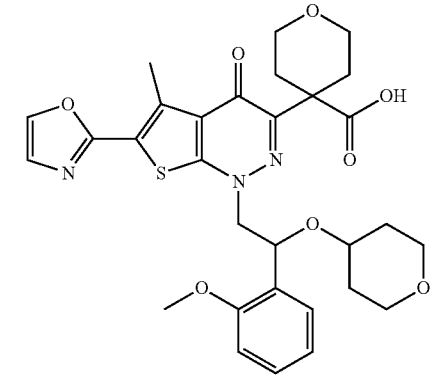 [SMILES: COc1ccccc1C(Cn1nc(C2(C(=O)O)CCOCC2)c(=O)c2c(C)c(-c3ncco3)sc21)OC1CCOCC1] | WX008 |
| | | 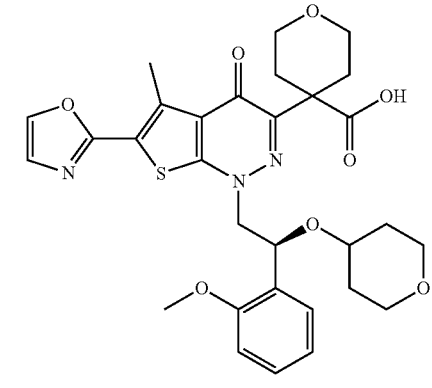 [SMILES: COc1ccccc1[C@@H](Cn1nc(C2(C(=O)O)CCOCC2)c(=O)c2c(C)c(-c3ncco3)sc21)OC1CCOCC1] | WX008A or WX008B |
| | | 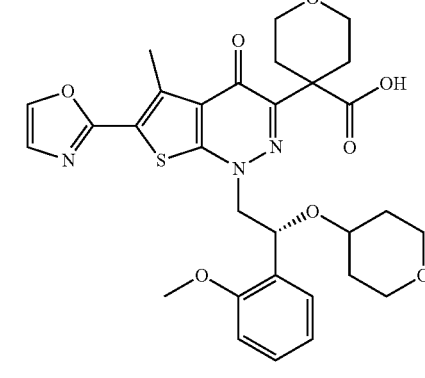 | WX008B or WX008A |
| 9 | 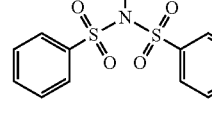 | 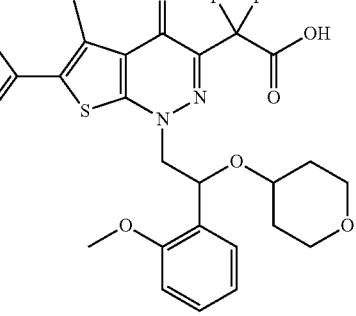 | WX009 |

TABLE 1-continued

Compound structure of each example

| Example | Halide fragment | Structure | Compound |
|---|---|---|---|
| | | | WX009A or WX009B |
| | | | WX009B or WX009A |
| 10 | (ClCH₂CH₂)₂N-Cbz | 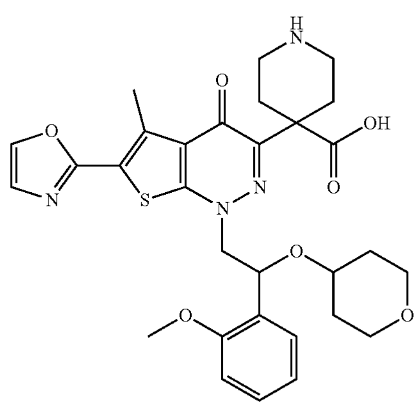 [SMILES: COc1ccccc1C(Cn1nc(C2(C(=O)O)CCNCC2)c(=O)c2c(C)c(-c3ncco3)sc21)OC1CCOCC1] | WX010 |
| 16 | MeI; The methoxybenzene in BB-3 intermediate was replaced with p-fluoromethoxybenzene | 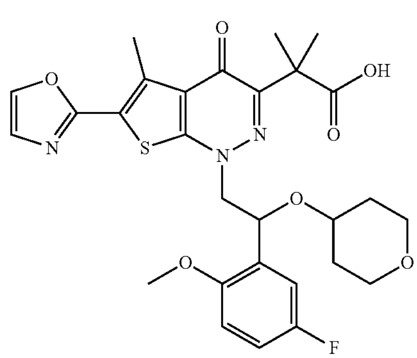 [SMILES: COc1ccc(F)cc1C(Cn1nc(C(C)(C)C(=O)O)c(=O)c2c(C)c(-c3ncco3)sc21)OC1CCOCC1] | WX016 |

TABLE 1-continued

Compound structure of each example

| Example | Halide fragment | Structure | Compound |
|---|---|---|---|
|  |  | (structure) | WX016A or WX016B |
|  |  | (structure) | WX016B or WX016A |

TABLE 2

NMR and MS data of each example

| Example | Compound | NMR | MS m/z: |
|---|---|---|---|
| 1 |  | SFC detection method: Column: Chiralpak AD-3 100 × 4.6 mm I.D., 3 μm; mobile phase: A: supercritical carbon dioxide, B: 0.05% diethylamine in ethanol; gradient: B from 5% to 40% in 4.5 minutes, 40% for 2.5 minutes, back to 5% equilibrium for 1 minute; flow rate: 2.8 mL/min; column temperature: 40° C.; wavelength: 220 nm. |  |
|  | WX001 | $^1$H NMR (400 MHz, CDCl$_3$) δ 7.69 (s, 1H), 7.47-7.45 (m, 1H), 7.26-7.24 (m, 1H), 7.20 (s, 1H), 6.99-6.95 (m, 1H), 6.84-6.82 (m, 1H), 5.42-5.38 (m, 1H), 4.38-4.34 (m, 1H), 4.13-4.07 (m, 1H), 3.80 (s, 3H), 3.70-3.60 (m, 1H), 3.47-3.38 (m, 1H), 3.35-3.08 (m, 3H), 2.95 (s, 3H), 2.40-2.29 (m, 2H), 2.20-2.15 (m, 2H), 1.77-1.75 (m, 2H), 1.62-1.48 (m, 5H), 1.12-1.09(m, 1H). A pair of racemates, with a ratio of 1:1, detected by SFC. | 580.1 (M + H)$^+$ |
|  | WX001A | SFC retention time 3.954 min<br>$^1$H NMR (400 MHz, CDCl$_3$,) δ 7.70 (s, 1H), 7.47-7.44 (m, 1H), 7.26-7.25 (m, 1H), 7.20 (s, 1H), 6.99-6.97 (m, 1H), 6.85-6.83 (m, 1H), 5.42-5.38 (m, 1H), 4.40-4.35 (m, 1H), 4.14-4.08 (m, 1H), 3.81 (s, 3H), 3.71-3.62 (m, 1H), 3.46-3.41 (m, 1H), 3.31-3.25 (m, 1H), 3.24-3.18 (m, 1H), 3.11-3.17 (m, 1H), 2.96 (s, 3H), 2.43-2.40 (m, 2H), 2.17-2.16 (m, 2H), 1.78-1.70 (m, 2H), 1.62-1.49 (m, 3H), 1.48-1.46 (m, 2H), 1.12-1.08 (m, 1H). |  |
|  | WX001B | SFC retention time 4.388 min<br>$^1$H NMR (400 MHz, CDCl$_3$) δ 7.70 (s, 1H), 7.46-7.44 (m, 1H), 7.27-7.24 (m, 1H), 7.20 (s, 1H), 6.99-6.97 (m, 1H), 6.85-6.83 (m, 1H), 5.41-5.38 (m, 1H), 4.39-4.35 (m, 1H), 4.14-4.08 (m, 1H), 3.81 (s, 3H), 3.71-3.62 (m, 1H), 3.46-3.41 (m, 1H), 3.31-3.25 (m, 1H), 3.24-3.18 (m, 1H), 3.11-3.17 (m, 1H), 2.96 (s, 3H), 2.42-2.40 (m, 2H), 2.18-2.16 (m, 2H), 1.77-1.75 (m, 2H), 1.62-1.58 (m, 3H), 1.48-1.46 (m, 2H), 1.11-1.08 (m, 1H). |  |

TABLE 2-continued

NMR and MS data of each example

| Example | Compound | NMR | MS m/z: |
|---|---|---|---|
| 2 | WX002 | $^1$H NMR (400 MHz, CDCl$_3$) δ7.79 (s, 1H), 7.58-7.56 (m, 1H), 7.38-7.34 (m, 1H), 7.30 (s, 1H), 7.21 (bs, 1H), 7.08-7.04 (m, 1H), 6.94-6.92 (m, 1H), 5.52-5.48 (m, 1H), 5.39 (bs, 1H), 4.50-4.45 (m, 1H), 4.18-4.12 (m, 1H), 3.93 (s, 3H), 3.84-3.82 (m, 2H), 3.75-3.67 (m, 1H), 3.54-3.45 (m, 1H), 3.39-3.36 (m, 1H), 3.35-3.22 (m, 2H), 3.06 (s, 3H), 1.71-1.72 (m, 1H), 1.59-1.50 (m, 2H), 1.18-1.15 (m, 1H). | 525.1 (M + H)$^+$ |
| 3 | | SFC detection method: column: Chiralcel OJ-3 100 × 4.6 mm I.D., 3 μm; mobile phase: A: supercritical carbon dioxide, B: 0.05% diethylamine in methanol; gradient: B from 5% to 40% in 4.5 minutes, 40% for 2.5 minutes, back to 5% equilibrium for 1 minute; flow rate: 2.8 mL/min; column temperature: 40° C.; wavelength: 220 nm. | |
| | WX003 | The crude product was directly purified by SFC. As racemates with a ratio of 1:1, detected by SFC. | 525.9 (M + H)$^+$ |
| | WX003A | SFC retention time 2.343 min<br>$^1$H NMR (400 MHz, CDCl$_3$) δ 7.73 (s, 1H), 7.47-7.45 (m, 1H), 7.28-7.26 (m, 1H), 7.22 (s, 1H), 6.99-6.97 (m, 1H), 6.86-6.84 (m, 1H), 5.41-5.38 (m, 1H), 4.43-4.39 (m, 1H), 4.15-4.09 (m, 1H), 3.91 (s, 2H), 3.84 (s, 3H), 3.68-3.60 (m, 1H), 3.48-3.40 (m, 1H), 3.35-3.26 (m, 1H), 3.25-3.12 (m, 2H), 2.98 (s, 3H), 1.61-1.57 (m, 1H), 1.52-1.41 (m, 2H), 1.08-1.05 (m, 1H). | |
| | WX003B | SFC retention time 2.685 min<br>$^1$H NMR (400 MHz, CDCl$_3$) δ 7.72 (s, 1H), 7.48-7.46 (m, 1H), 7.28-7.26 (m, 1H), 7.22 (s, 1H), 6.99-6.95 (m, 1H), 6.86-6.84 (m, 1H), 5.41-5.38 (m, 1H), 4.42-4.38 (m, 1H), 4.14-4.09 (m, 1H), 3.89 (s, 2H), 3.84 (s, 3H), 3.68-3.60 (m, 1H), 3.48-3.40 (m, 1H), 3.35-3.26 (m, 1H), 3.25-3.12 (m, 2H), 2.97 (s, 3H), 1.61-1.60 (m, 1H), 1.49-1.42 (m, 2H), 1.08-1.06 (m, 1H). | |
| 4 | | SFC detection method: column: Chiralpak AD-3 100 × 4.6 mm I.D., 3 μm; mobile phase: A: supercritical carbon dioxide, B: 0.05% diethylamine in ethanol; gradient: B from 5% to 40% in 2.5 minutes, 40% for 2 minutes, back to 5% equilibrium for 1 minute. Flow rate: 2.5 mL/min; column temperature: 40° C.; wavelength: 220 nm. | |
| | WX004 | The crude product obtained after hydrogenation was directly separated by SFC to give the enantiomers. As racemates with a ratio of 1:1, detected by SFC. | 554.0 (M + H)$^+$ |
| | WX004A | SFC retention time 3.636 min<br>$^1$H NMR (400 MHz, CDCl$_3$) δ 7.69 (s, 1H), 7.47-7.45 (m, 1H), 7.26-7.24 (m, 1H), 7.22 (s, 1H), 6.98-6.94 (m, 1H), 6.84-6.82 (m, 1H), 5.42-5.40 (m, 1H), 4.38-4.34 (m, 1H), 4.15-4.10 (m, 1H), 3.78 (s, 3H), 3.71-3.63 (m, 1H), 3.50-3.42 (m, 1H), 3.35-3.32 (m, 1H), 3.28-3.13 (m, 2H), 2.95 (s, 3H), 1.64-1.62 (m, 1H), 1.54-1.43 (m, 8H), 1.16-1.14 (m, 1H). | |
| | WX004B | SFC retention time 3.940 min<br>$^1$H NMR (400 MHz, CDCl$_3$) δ 7.69 (s, 1H), 7.47-7.45 (m, 1H), 7.26-7.24 (m, 1H), 7.22 (s, 1H), 6.98-6.95 (m, 1H), 6.84-6.82 (m, 1H), 5.43-5.40 (m, 1H), 4.39-4.34 (m, 1H), 4.15-4.10 (m, 1H), 3.78 (s, 3H), 3.71-3.63 (m, 1H), 3.50-3.42 (m, 1H), 3.35-3.32 (m, 1H), 3.28-3.13 (m, 2H), 2.95 (s, 3H), 1.64-1.62 (m, 1H), 1.54-1.43 (m, 8H), 1.19-1.16 (m, 1H). | |
| 5 | WX005 | $^1$H NMR (400 MHz, CDCl$_3$) δ 7.71 (s, 1H), 7.45-7.42 (m, 1H), 7.29-7.24 (m, 1H), 7.21 (s, 1H), 6.99-6.93 (m, 1H), 6.86-6.80 (m, 1H), 5.36-5.34 (m, 1H), 4.39-4.36 (m, 1H), 4.18-4.10 (m, 1H), 3.82 (s, 3H), 3.69-3.63 (m, 1H), 3.49-3.42 (m, 1H), 3.34-3.31 (m, 1H), 3.26-3.13 (m, 2H), 2.98 (s, 3H), 1.61-1.55 (m, 2H), 1.47-1.42 (m, 2H), 1.20-1.12 (m, 4H). | 552.1 (M + H)$^+$ |
| 6 | WX006 | $^1$H NMR (400 MHz, CDCl$_3$) δ 7.81 (s, 1H), 7.52-7.51 (m, 1H), 7.37-7.31 (m, 1H), 7.31 (s, 1H), 7.07-7.03 (m, 1H), 6.93-6.91 (m, 1H), 5.52-5.48 (m, 1H), 4.54-4.50 (m, 1H), 4.30-4.24 (m, 1H), 3.88 (s, 3H), 3.78-3.69 (m, 1H), 3.58-3.51 (m, 1H), 3.45-3.37 (m, 1H), 3.36-3.21 (m, 2H), 3.05 (s, 3H), 3.00-2.89 (m, 2H), 2.68-2.56 (m, 2H), 2.21-2.09 (m, 1H), 1.83-1.81 (m, 1H), 1.72-1.70 (m, 2H), 1.51-1.48 (m, 1H), 1.24-1.17 (m, 1H). | 566.2 (M + H)$^+$ |

TABLE 2-continued

| | | NMR and MS data of each example | |
|---|---|---|---|
| Example | Compound | NMR | MS m/z: |
| 7 | | SFC detection method: Column: Chiralpak AD-3 50 × 3 mm I.D., 3 µm; mobile phase: A: supercritical carbon dioxide, B: 0.05% diethylamine in isopropanol; gradient: B from 5% to 40% within 2.5 minutes, 40% for 0.35 min, from 40% back to 5% in 0.15 minute. Flow rate: 2.5 mL/min; column temperature: 40° C.; Wavelength: 220 nm. | |
| | WX007 | The crude product was directly separated by SFC to give the enantiomers. As racemates with a ratio of 1:1, detected by SFC. | 594.0 (M + H)+ |
| | WX007A | SFC retention time 1.875 min<br>$^1$H NMR (400 MHz, CDCl$_3$) δ 7.71 (s, 1H), 7.47-7.45 (m, 1H), 7.30-7.25 (m, 1H), 7.21 (s, 1H), 6.99-6.96 (m, 1H), 6.85-6.83 (m, 1H), 5.45-5.42 (m, 1H), 4.43-4.38 (m, 1H), 4.15-4.10 (m, 1H), 3.80 (s, 3H), 3.68-3.64 (m, 1H), 3.47-3.42 (m, 1H), 3.34-3.30 (m, 1H), 3.27-3.20 (m, 1H), 3.19-3.12 (m, 1H), 2.96 (s, 3H), 2.17-2.05 (m, 4H), 1.69-1.63 (m, 2H), 1.53-1.45 (m, 5H), 1.32-1.41 (m, 2H), 1.12-1.09 (m, 1H). | |
| | WX007B | SFC retention time 2.177 min<br>$^1$H NMR (400 MHz, CDCl$_3$) δ 7.80 (s, 1H), 7.56-7.54 (m, 1H), 7.39-7.33 (m, 1H), 7.30 (s, 1H), 7.09-7.04 (m, 1H), 6.94-6.92 (m, 1H), 5.54-5.51 (m, 1H), 4.52-4.48 (m, 1H), 4.22-4.19 (m, 1H), 3.89 (s, 3H), 3.79-3.72 (m, 1H), 3.56-3.51 (m, 1H), 3.45-3.37 (m, 1H), 3.35-3.29 (m, 1H), 3.27-3.21 (m, 1H), 3.05 (s, 3H), 2.26-2.07 (m, 4H), 1.74-1.73 (m, 2H), 1.65-1.54 (m, 5H), 1.51-1.47 (m, 2H), 1.23-1.17 (m, 1H). | |
| 8 | | SFC detection method: column: Chiralpak AD-3 100 × 4.6 mm I.D., 3 µm; mobile phase: A: supercritical carbon dioxide, B: 0.05% diethylamine in isopropanol; gradient: B from 5% to 40% in 2.5 minutes, 40% for 0.35 minute, from 40% to 5% in 0.15 minute. Flow rate: 2.5 mL/min; column temperature: 40° C.; wavelength: 220 nm. | |
| | WX008 | The crude product was directly separated by SFC to give the enantiomers. As racemates with a ratio of 1:1, detected by SFC. | 596.1 (M + H)+ |
| | WX008A | SFC retention time 2.017 min<br>$^1$H NMR (400 MHz, CDCl$_3$) δ 7.72 (s, 1H), 7.46-7.44 (m, 1H), 7.31-7.26 (m, 1H), 7.22 (s, 1H), 7.00-6.96 (m, 1H), 6.86-6.84 (m, 1H), 5.43-5.40 (m, 1H), 4.44-4.39 (m, 1H), 4.18-4.13 (m, 1H), 3.86-3.79 (m, 5H), 3.79-3.61 (m, 4H), 3.48-3.42 (m, 1H), 3.34-3.30 (m, 1H), 3.27-3.14 (m, 2H), 2.95 (s, 3H), 2.48-2.41 (m, 2H), 2.21-2.11 (m, 2H), 1.66-1.62 (m, 1H), 1.48-1.45 (m, 2H), 1.12-1.03 (m, 1H). | |
| | WX008B | SFC retention time 2.336 min<br>$^1$H NMR (400 MHz, CDCl$_3$) δ 7.72 (s, 1H), 7.47-7.44 (m, 1H), 7.32-7.26 (m, 1H), 7.22 (s, 1H), 7.00-6.96 (m, 1H), 6.86-6.84 (m, 1H), 5.43-5.38 (m, 1H), 4.45-4.40 (m, 1H), 4.16-4.14 (m, 1H), 3.86-3.82 (m, 1H), 3.80 (s, 3H), 3.49-3.43 (m, 1H), 3.34-3.30 (m, 1H), 3.26-3.20 (m, 1H), 3.19-3.12 (m, 1H), 2.95 (s, 3H), 2.43-2.41 (m, 2H), 2.16-2.14 (m, 2H), 1.67-1.65 (m, 1H), 1.57-1.45 (m, 2H), 1.12-1.06 (m, 1H). | |
| 9 | | SFC detection method: column: Chiralcel AD-3 100 × 4.6 mm I.D., 3 µm; mobile phase: A: supercritical carbon dioxide, B: 0.05% diethylamine in ethanol; gradient: B from 5% to 40% in 4.5 minutes, 40% for 2.5 minutes, back to 5% equilibrium for 1 minute; flow rate: 2.8 mL/min; column temperature: 40° C.; wavelength: 220 nm. | |
| | WX009 | The crude product was directly separated by SFC to give the enantiomers. As racemates with a ratio of 1:1, detected by SFC. | 562.1 (M + H)+ |
| | WX009A | SFC retention time is 3.273 min.<br>$^1$H NMR (400 MHz, CDCl$_3$,) δ 7.63 (s, 1H), 7.45-7.49 (m, 1H), 7.25-7.21 (m, 1H), 7.12 (s, 1H), 6.95-6.91 (m, 1H), 6.81-6.79 (m, 1H), 5.41-5.39 (m, 1H), 4.40-4.37 (m, 1H), 4.14-4.13 (m, 1H), 3.79 (s, 3H), 3.64-3.59 (m, 1H), 3.42 (s, 3H), 3.30-3.28 (m, 1H), 3.19-3.12 (m, 1H), 2.82-2.78 (m, 2H), 1.57-1.49 (m, 2H), 1.41-1.39 (m, 1H), 1.19-1.17 (m, 1H). | |

TABLE 2-continued

NMR and MS data of each example

| Example | Compound | NMR | MS m/z: |
|---|---|---|---|
| | WX009B | SFC retention time is 3.674 min.<br>$^1$H NMR (400 MHz, CDCl$_3$) δ 7.77 (s, 1H), 7.56-7.54 (m, 1H), 7.37-7.34 (m, 1H), 7.25 (s, 1H), 7.04-7.02 (m, 1H), 6.93-6.91 (m, 1H), 5.53-5.51 (m, 1H), 4.55-4.52 (m, 1H), 4.30-4.25 (m, 1H), 3.90 (s, 3H), 3.75-3.70 (m, 1H), 3.60-3.58 (m, 1H), 3.45-3.39 (m, 1H), 3.31-3.25 (m, 1H), 2.96 (s, 3H), 3.30-3.28 (m, 1H), 3.19-3.12 (m, 1H), 2.82-2.78 (m, 2H), 1.57-1.41 (m, 2H), 1.25-1.17 (m, 1H). | |
| 10 | WX010 | $^1$H NMR (400 MHz, DMSO-d$_6$) δ 8.76-8.70 (d, 1H), 8.30 (s, 1H), 7.51-7.49 (m, 1H), 7.46 (s, 1H), 7.38-7.34 (m, 1H), 7.08-7.05 (m, 2H), 5.41-5.38 (m, 1H), 4.50-4.45 (m, 1H), 4.25-4.19 (m, 1H), 3.88 (s, 3H), 3.63-3.59 (m, 1H), 3.28-3.15 (m, 5H), 3.14-3.08 (m, 2H), 2.90 (s, 3H), 2.39-2.21 (m, 4H), 1.70-1.62 (m, 1H), 1.57-1.48 (m, 1H), 1.40-1.34 (m, 1H), 1.22-1.17 (m, 1H), 1.05-0.94 (m, 1H) | 595.1 (M + H)$^+$ |
| 16 | | SFC detection method: column: Lux 3u Cellulose-2 150*4.6 mm I.D., 3 μm; mobile phase: A: supercritical carbon dioxide, B: 0.05% diethylamine in ethanol; gradient: B from 5% to 40% in 4.5 minutes, 40% for 2.5 minutes, back to 5% equilibrium for 1 minute; flow rate: 2.5 mL/min; column temperature: 40° C.; wavelength: 220 nm. | 572.1 (M + H)$^+$ |
| | WX016A | The SFC retention time is 3.725 min.<br>$^1$H NMR (400 MHz, CDCl$_3$) δ 7.69 (s, 1H), 7.20-7.22 (m, 2H), 6.93-6.91 (m, 1H), 6.77-6.73 (m, 1H), 5.37-5.36 (m, 1H), 4.40-4.33 (m, 1H), 4.13-4.10 (m, 1H), 3.75 (s, 3H), 3.70-3.67 (m, 1H), 3.48-3.43 (m, 1H), 3.32-3.17 (m, 3H), 2.94 (s, 3H), 1.68-1.62 (m, 1H), 1.59-1.53 (m, 1H), 1.50 (s, 3H), 1.45 (s, 3H), 1.18-1.13 (m, 1H), 0.83-0.79 (m, 1 H). | |
| | WX016B | The SFC retention time is 6.972 min.<br>$^1$H NMR (400 MHz, CDCl$_3$) δ7.74 (s, 1H), 7.24-7.23 (m, 2H), 7.00-6.97 (m, 1H), 6.82-6.79 (m, 1H), 5.44-5.41 (m, 1H) 4.41-4.37 (m, 1H), 4.17-4.14 (m, 1H), 3.81 (s, 3 H), 3.76-3.73 (m, 1H), 3.56-3.49 (m, 1H), 3.39-3.23 (m, 3H), 2.97 (s, 3H) 1.73-1.70 (m, 1H), 1.66-1.59 (m, 1H), 1.54 (s, 3H), 1.49 (s, 3H), 1.25-1.16 (m, 1H) 0.83-0.85 (m, 1H). | |

Example 11: WX011

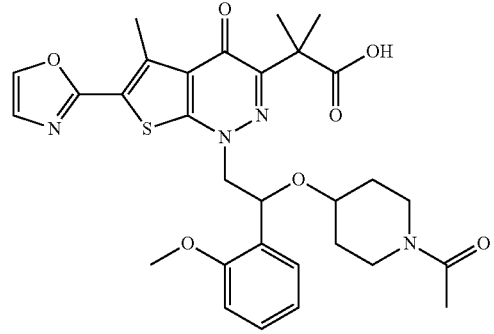

WX011

Synthetic Route

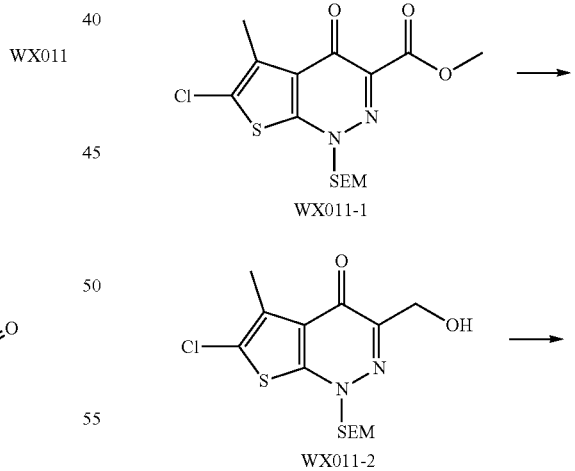

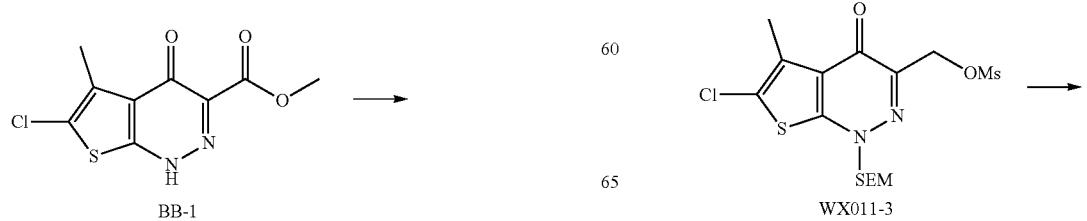

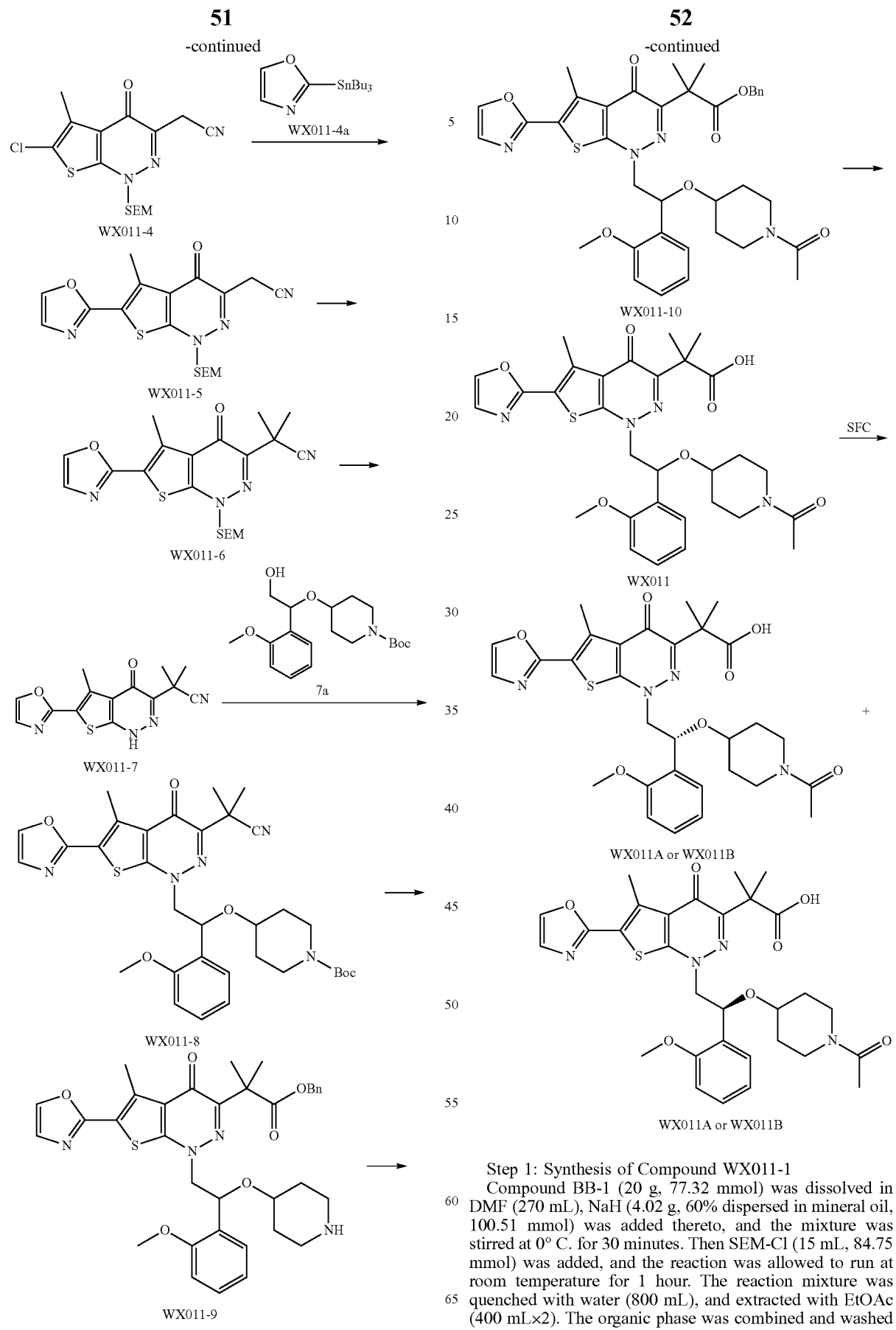

Step 1: Synthesis of Compound WX011-1

Compound BB-1 (20 g, 77.32 mmol) was dissolved in DMF (270 mL), NaH (4.02 g, 60% dispersed in mineral oil, 100.51 mmol) was added thereto, and the mixture was stirred at 0° C. for 30 minutes. Then SEM-Cl (15 mL, 84.75 mmol) was added, and the reaction was allowed to run at room temperature for 1 hour. The reaction mixture was quenched with water (800 mL), and extracted with EtOAc (400 mL×2). The organic phase was combined and washed with saturated brine (100 mL×4), dried over anhydrous sodium sulfate, filtered, and the solvent was removed under reduced pressure. The resulting residue was separated by chromatography column to give the target compound WX011-1.

$^1$HNMR (400 MHz, CDCl$_3$) δ 5.52 (s, 2H), 3.99 (s, 3H), 3.66-3.62 (m, 2H) 2.59 (s, 3H), 1.00-0.96 (m, 2H), 0.00 (s, 9H).

Step 2: Synthesis of Compound WX011-2

Compound WX011-1 (10 g, 25.71 mmol) was dissolved in methanol (100 mL), lithium borohydride (2.8 g, 128.55 mmol) was added thereto, and the reaction was allowed to run at room temperature for 2 hours. The reaction mixture was quenched with water (200 mL) and the methanol was removed under reduced pressure. The mixture was extracted with EtOAc (300 mL×2), and the organic phase was combined, washed with saturated brine (50 mL×2), dried over anhydrous sodium sulfate, and filtered. The solvent was removed under reduced pressure, and the resulting residue was used directly in the next step. $^1$HNMR (400 MHz, CDCl$_3$) δ 5.48 (s, 2H), 4.77 (s, 2H), 3.64-3.60 (m, 2H), 2.58 (s, 3H), 1.00-0.95 (m, 2H), 0.01 (s, 9H).

Step 3: Synthesis of Compound WX011-3

Compound WX011-2 (8 g, 22.16 mmol) and triethylamine (6.2 mL, 44.33 mmol) were dissolved in DCM (100 mL), MsCl (2.3 mL, 29.68 mmol) was added thereto at 0° C., and the reaction was allowed to run for 1 hour after the addition was completed. The reaction mixture was quenched with ice water (100 mL), and extracted with DCM (60 mL×2). The organic phase was combined, dried over anhydrous sodium sulfate, filtered, and the solvent was removed under reduced pressure. The resulting residue was used directly used in the next step.

Step 4: Synthesis of Compound WX011-4

Compound WX011-3 (8.5 g, 19.36 mmol) was dissolved in DMF (100 mL), NaCN (4.07 g, 83.04 mmol) was added thereto, and the reaction was allowed to run at room temperature for 2 hours. After the completion of the reaction, the reaction was quenched by water (200 mL) and extracted with EtOAc (200 mL×3). The organic phase was combined, washed with saturated brine (100 mL×4), dried over anhydrous sodium sulfate, filtered, and the solvent was removed under reduced pressure. The resulting residue was separated by chromatography column to give the target compound WX011-4. $^1$HNMR (400 MHz, DMSO-d$_6$) δ 5.51 (s, 2H), 3.90 (s, 2H), 3.66-3.62 (m, 2H), 2.56 (s, 3H), 0.99-0.95 (m, 2H), 0.00 (s, 9H).

Step 5: Synthesis of Compound WX011-5

Compound WX011-4 (2.5 g, 6.76 mmol), 2-(tri-n-butylstannyl)oxazole (6.05 g, 16.89 mmol) were dissolved in toluene (30 mL), and tetrakis(triphenylphosphine)palladium (1.56 g, 1.35 mmol) was added thereto. The reaction mixture was purged with nitrogen for 3 times and raised to 120° C., and the reaction was allowed to run for 4 hours. After cooling to room temperature, the reaction was quenched with saturated potassium fluoride (20 mL). Water (80 mL) was added and extracted with EtOAc (100 mL×2). The organic phase were combined, dried over anhydrous sodium sulfate, filtered, and the solvent was removed under reduced pressure. The residue was separated by chromatography column to give the target compound WX011-5. $^1$HNMR (400 MHz, CDCl$_3$) δ 7.77 (s, 1H), 7.29 (s, 1H), 5.60 (s, 2H), 3.94 (s, 2H), 3.71-3.67 (m, 2H), 3.02 (s, 3H), 1.02-0.98 (m, 2H), 0.01 (s, 9H).

Step 6: Synthesis of Compound WX011-6

Compound WX011-5 (1.9 g, 4.72 mmol) and methyl iodide (1.6 mL, 25.50 mol) were dissolved in THF (20 mL), potassium tert-butoxide solution (1 M, 14.2 mL, 14.2 mmol) was added dropwise at 0° C., and the reaction was allowed to run at room temperature for 1 hour. The reaction was quenched with water (100 mL), and extracted with EtOAc (100 mL×2). The organic phase was combined, dried over anhydrous sodium sulfate, filtered to remove the desiccant, and the solvent was removed under reduced pressure. The residue was used directly in the next step. $^1$HNMR (400 MHz, CDCl$_3$) δ 7.75 (s, 1H), 7.29 (s, 1H), 5.54 (s, 2H), 3.70-3.65 (m, 2H), 3.02 (s, 3H), 1.64 (s, 6H), 1.00-0.96 (m, 2H), 0.01 (s, 9H).

Step 7: Synthesis of Compound WX011-7

Compound WX011-6 (1 g, 2.32 mmol) was added to a solution of TBAF (1 M, 15 mL, 15 mmol) in THF, and the reaction was allowed to run at room temperature for 1 hour. After the completion of the reaction, the reaction was quenched with water (80 mL), and extracted with EtOAc (100 mL×2). The combined organic phase was washed with water (50 mL×5), dried over anhydrous sodium sulfate, filtered to remove the desiccant, and the solvent in the filtrate was removed under reduced pressure. The resulting residue was directly used in the next step. $^1$HNMR (400 MHz, CDCl$_3$) δ 7.72 (s, 1H), 7.24 (s, 1H), 2.95 (s, 3H), 1.81 (s, 6H).

Step 8: Synthesis of Compound WX011-8

Compound WX011-7 (0.56 g, 1.86 mmol), compound WX011-7a (786 mg, 2.24 mmol) and triphenylphosphine (978 mg, 3.73 mmol) were added to THF (10 mL), DIAD was added thereto at 0° C. (730 μL, 3.75 mmol), and the reaction was allowed to run at room temperature for 15 hours. After the completion of the reaction, the solvent was removed under reduced pressure, and the resulting residue was directly used in the next step. LCMS: [M+Na]=656.2.

Step 9: Synthesis of Compound WX011-9

Compound WX011-8 (0.9 g, 1.42 mmol) was dissolved in benzyl alcohol (15 mL), a solution of hydrogen chloride in 1,4-dioxane (4 M, 15 mL) was added thereto, and the reaction was allowed to run at 50° C. for 1 hour. After the completion of the reaction, the solvent was removed under reduced pressure, and the resulting residue was slurried with methyl tert-butyl ether (150 mL) to give the target compound WX011-9. LCMS: [M+H]$^+$=643.4.

Step 10: Synthesis of Compound WX011-10

DCM (0.7 mL) was added to compound WX011-9 (0.1 g, 155.58 μmol), sodium hydroxide (1 M, 0.8 mL) was added, followed by acetyl chloride (44 μL, 622 μmol), and then the reaction was allowed to run at room temperature for 1 hour. The reaction mixture was extracted with DCM (5 mL×2). The combined organic phase was dried over anhydrous sodium sulfate, filtered to remove the desiccant, and the solvent was removed from the filtrate under reduced pressure. The resulting residue was separated by preparative chromatography (hydrochloric acid condition) to give the target compound WX011-10. LCMS: [M+H]$^+$=707.1.

Step 11: Synthesis of Compound WX011

Compound WX011-10 (50 mg, 73.01 μmol) was dissolved in MeOH (5 mL), 10% Pd/C (100 mg) was added under nitrogen atmosphere. The reaction system was purged with hydrogen for 3 times, and then the reaction was allowed to run under hydrogen atmosphere (15 Psi) at room temperature for 1 hour. The reaction mixture was filtered, and the solvent was removed under reduced pressure to give a residue. The residue was separated by preparative chromatography (hydrochloric acid condition) to give the target compound WX011.

Compound WX011 was analyzed by supercritical fluid chromatography (column: (S,S)Whelk-01, 100×4.6 mm 5 μm; mobile phase: A: supercritical carbon dioxide, B: 0.05% diethylamine in methanol; gradient: B from 5% to 40% in 4.5 minutes, 40% for 2.5 minutes, back to 5% equilibrium for 1 minute; flow rate: 2.8 mL/min; column temperature: 40° C.; wavelength: 220 nm) as racemates. Chiral isomers WX011A and WX011B were separated, and their retention times were 3.078 min and 3.734 min, respectively.

WX011A, ¹HNMR (400 MHz, CDCl₃) δ 7.70 (s, 1H), 7.47-7.42 (m, 1H), 7.30-7.26 (m, 2H), 6.99-6.96 (m, 1H), 6.86-6.84 (m, 1H), 5.47-5.42 (m, 1H), 4.39-4.30 (m, 1H), 4.15-4.10 (m, 1H), 3.82 (s, 3H), 3.47-3.00 (m, 5H), 2.95 (s, 3H), 1.93, 1.91 (2 s, 3H), 1.54-1.19 (m, 10H); LCMS (5-95 AB/1.5 min): Rt=0.904; [M+Na]=617.3.

WX011B, ¹HNMR (400 MHz, CDCl₃) δ 7.70 (s, 1H) 7.47-7.42 (m, 1H) 7.30-7.26 (m, 2H) 6.99-6.96 (m, 1H) 6.86-6.84 (m, 1H) 5.47-5.42 (m, 1H) 4.39-4.33 (m, 1H) 4.15-4.10 (m, 1H) 3.82 (s, 3H) 3.47-3.00 (m, 5H) 2.95 (s, 3H) 1.93, 1.91 (2 s, 3H) 1.54-1.19 (m, 10H); LCMS (5-95 AB/1.5 min): Rt=0.904; [M+Na]=617.4.

Referring to the synthetic methods of steps 10 and 11 in the example 1, each example in the following table was synthesized using different intermediate fragments in step 10. The structures in the table also represent their possible isomers.

TABLE 3

Compound structure of each example

| Example | Intermediate fragment | Structure | Compound |
|---|---|---|---|
| 12 | 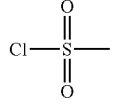 | 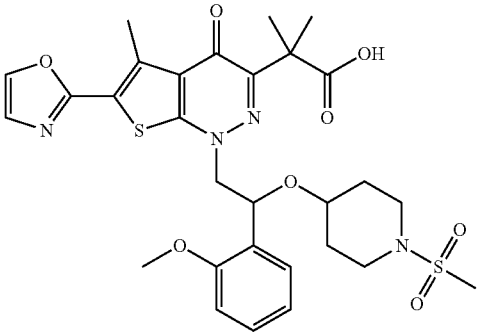 [SMILES: COc1ccccc1C(Cn1nc(C(C)(C)C(=O)O)c(=O)c2c(C)c(-c3ncco3)sc21)OC1CCN(S(C)(=O)=O)CC1] | WX012 |
|  |  | 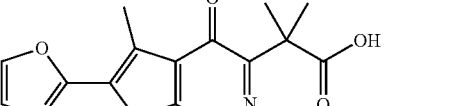 | WX012A or WX012B |
|  |  | 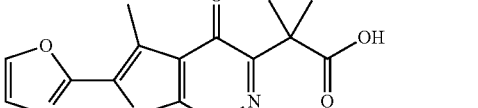 | WX012B or WX012A |

TABLE 3-continued

Compound structure of each example

| Example | Intermediate fragment | Structure | Compound |
|---|---|---|---|
| 13 | MeI | 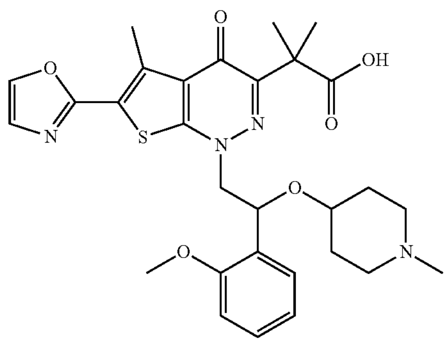 [SMILES: COc1ccccc1C(Cn1nc(C(C)(C)C(=O)O)c(=O)c2c(C)c(-c3ncco3)sc21)OC1CCN(C)CC1] | WX013 |
| 14 | (tert-butyl chloroformate) | 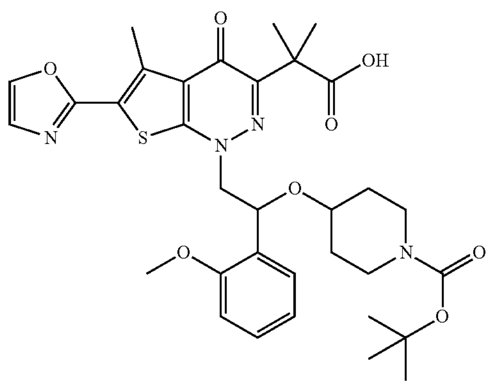 [SMILES: COc1ccccc1C(Cn1nc(C(C)(C)C(=O)O)c(=O)c2c(C)c(-c3ncco3)sc21)OC1CCN(C(=O)OC(C)(C)C)CC1] | WX014 |
| 15 | (methyl chloroformate) | 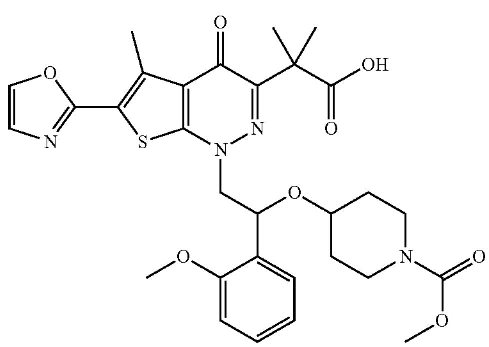 [SMILES: COC(=O)N1CCC(OC(Cn2nc(C(C)(C)C(=O)O)c(=O)c3c(C)c(-c4ncco4)sc32)c2ccccc2OC)CC1] | WX015 |
|  |  |  | WX015A or WX015B |

TABLE 3-continued

Compound structure of each example

| Example | Intermediate fragment | Structure | Compound |
|---|---|---|---|
|  |  |  | WX015B or WX015A |

TABLE 4

NMR and MS data of each example

| Example | Compound | NMR | MS m/z: |
|---|---|---|---|
| 12 |  | SFC detection method: Column: (S,S)Whelk-01, 100 × 4 6 mm I.D., 5 μm; mobile phase: A: supercritical carbon dioxide, B: 0.05% diethylamine in methanol; gradient: B from 5% to 40% in 4.5 minutes, 40% for 2.5 minutes, back to 5% equilibrium for 1 minute; flow rate: 2.5 mL/min; column temperature: 40° C.; wavelength: 220 nm. |  |
|  | WX012 WX012A | A pair of racemates with a ratio of 1:1, detected by SFC. SFC retention time 2.649 min $^1$H NMR (400 MHz, CDCl$_3$) δ 7.70 (s, 1H) 7.41-7.39 (m, 1H) 7.28-7.26 (m, 2H) 6.99-6.95 (m, 1H) 6.87-7.85 (m, 1H) 5.43-5.41 (m, 1H) 4.40-4.37 (m, 1 H) 4.11-4.06 (m, 1H) 3.83 (s, 3H) 3.45-3.41 (m, 1 H) 3.15-3.00 (m, 1H) 2.90 (s, 1H) 2.85-2.72 (m, 1 H) 2.39 (s, 3H) 2.30-2.27 (m, 1H) 1.66-1.18 (m, 10 H). | 631.1 (M + H)$^+$ |
|  | WX012B | SFC retention time 3.874 min $^1$H NMR (400 MHz, CDCl$_3$) δ 7.70 (s, 1H) 7.41-7.39 (m, 1 H) 7.28-7.26 (m, 2H) 6.99-6.95 (m, 1H) 6.87-7.85 (m, 1H) 5.43-5.41 (m, 1H) 4.40-4.37 (m, 1 H) 4.11-4.06 (m, 1H) 3.83 (s, 3H) 3.45-3.41 (m, 1 H) 3.15-3.00 (m, 1H) 2.90 (s, 1H) 2.85-2.72 (m, 1 H) 2.39 (s, 3H) 2.30-2.27 (m, 1H) 1.66-1.18 (m, 10 H). |  |
| 13 | WX013 | $^1$H NMR (400 MHz, CDCl$_3$) δ 7.84-7.82 (m, 1H), 7.45-7.30 (m, 3H), 7.10-7.09 (m, 1H), 7.0-6.98 (m, 1 H), 5.60-5.52 (m, 1H) 4.53-4.49 (m, 1H), 4.25-4.22 (m, 1H), 3.98-3.96 (m, 4H), 3.65-3.65 (m, 1 H), 3.03-2.99 (m, 5H), 2.65-2.35 (m, 4H), 1.70-1.50 (m, 10H). | 567.4 (M + H)$^+$ |
| 14 | WX014 | $^1$H NMR (400 MHz, CDCl$_3$) δ 7.70 (s, 1H) 7.44-7.43 (m, 1H) 7.26-7.20 (m, 2H) 6.99-6.95 (m, 1H) 6.84-7.82 (m, 1H) 5.42-5.41 (m, 1H) 4.38-4.34 (m, 1 H) 4.18-4.12 (m, 1H) 3.80 (s, 3H) 3.45-3.42 (m, 1 H) 3.29-3.19 (m, 1H) 2.96 (s, 3 H) 2.95-2.85 (m, 2 H) 1.52 (s, 3H) 1.50 (s, 3H) 1.35-1.31 (m, 3H) 1.18 (s, 9H) 1.04-1.03 (m, 1H). | 653.1 (M + H)$^+$ |
| 15 |  | SFC detection method: column: Chiralcel OJ-3, 100 × 4.6 mm I.D., 3 μm; mobile phase: A: supercritical carbon dioxide, B: 0.05% diethylamine in ethanol; gradient: B from 5% to 40% in 4.5 minutes, 40% for 2.5 minutes, back to 5% equilibrium for 1 minute; flow rate: 2.5 mL/min; column temperature: 40° C.; wavelength: 220 nm. |  |
|  | WX015 | The crude product obtained after hydrogenation was directly separated by SFC to give the enantiomers. As racemates with a ratio of 1:1, detected by SFC. | 611.4 (M + H)$^+$ |
|  | WX015A | SFC retention time 2.475 min $^1$H NMR (400 MHz, CDCl$_3$) δ 7.70 (s, 1H) 7.44 (d, J = 7.2 Hz, 1H) 7.28-7.20 (m, 2H) 7.00-6.95 (m, 1H) 6.85-7.83 (m, 1H) 5.43-5.41 (m, 1H) 4.38-4.34 (m, 1H) 4.16-4.11 (m, 1H) 3.80 (s, 3H) 3.55 (s, 3H) 3.45-3.05 (m, 5H) 2.96 (s, 1H) 1.60-1.10 (m, 10H). |  |

TABLE 4-continued

NMR and MS data of each example

| Example | Compound | NMR | MS m/z: |
|---|---|---|---|
| | WX015B | SFC retention time 2.658 min<br>$^1$H NMR (400 MHz, CDCl$_3$) δ 7.70 (s, 1H) 7.44 (d, J = 7.2 Hz, 1H) 7.28-7.20 (m, 2H) 7.00-6.95 (m, 1H) 6.85-7.83 (m, 1H) 5.43-5.41 (m, 1H) 4.38-4.34 (m, 1H) 4.16-4.11 (m, 1H) 3.80 (s, 3H) 3.55 (s, 3H) 3.45-3.05 (m, 5H) 2.96 (s, 1H) 1.60-1.10 (m, 10H). | |

Experimental Example 1: In Vitro Evaluation

Objective of this Experiment:

The IC$_{50}$ value was determined to evaluate the ability of the test compounds to inhibit acetyl-CoA carboxylase (ACC).

Experimental Materials:

Protein: human acetyl-CoA carboxylase 1 (hACC1) and human acetyl-CoA carboxylase 2 (hACC2).

Substrate: NaHCO$_3$

Cofactor: acetyl coenzyme A, ATP

Activator: potassium citrate

Experimental Method:

1. 1 time of the enzyme/substrate/cofactor was added to the wells of the well plate.

2. According to Acoustic technology, the solutions of the compounds in DMSO were added to the above enzyme mixture and the mixture was pre-incubated for 15 minutes.

3. ATP was added to initiate the reaction and the mixture was shaken until thoroughly mixed.

4. The mixture was incubated for 1 hour at room temperature.

5. After quenching the reaction, the incubation continued for 40 minutes.

6. After adding the detection reagents, the mixture was incubated for 30 minutes.

7. Measure Luminescence.

8. Data analysis: based on the standard curve of ADP, the luminescence was converted into ADP product concentration and the enzyme activity was calculated. Graphpad Prism software was used to fit the curve to obtain the IC$_{50}$ value. The experimental results are shown in Table 5.

TABLE 5

In vitro screening test results of the compounds of the present disclosure

| Compound | hACC1 (nM) | hACC2 (nM) |
|---|---|---|
| WX001B | 4.9 | 8 |
| WX002 | 53.6 | 8.7 |
| WX003B | 10.9 | 3.4 |
| WX004B | 14.1 | 10.3 |
| WX005 | 46.6 | 45 |
| WX006 | 20.3 | 22.1 |
| WX007B | 9.1 | 12.6 |
| WX008B | 5.3 | 13.9 |
| WX009B | 5.6 | 11 |
| WX010 | 83.9 | 70.7 |
| WX011 | 26 | 10.9 |
| WX012 | 14.2 | 5.7 |
| WX014 | 26 | 7.2 |
| WX015 | 20.2 | 7.0 |
| WX016B | 11.1 | 4.8 |

Conclusion: The compounds of the present disclosure have a strong inhibitory activity on human ACC1/ACC2 enzyme.

Experimental Example 2: Evaluation of the Pharmacokinetics Characteristics of the Compounds Objective of this Experiment:

Testing the pharmacokinetics characteristics of the compounds in C57BL/6 mice

Experimental Materials:

C57BL/6 mice (male, 18-30 g, 7-9 weeks, Shanghai Lingchang Biotechnology Co., Ltd.)

Experimental Operation:

The clear solution of the test compounds (0.5 mg/mL in 10% DMSO, 10% polyethylene glycol stearate, 80% water) was injected via tail vein into 4 male C57BL/6 mice (overnight fasted, 7-9 weeks), at a dose of 2.0 mg/kg. The suspensions or clear solutions of the test compounds (1 mg/mL in 10% PEG400, 90% (0.5% methylcellulose+0.2% Tween 80)) were administrated by oral gavage to 4 male C57BL/6 mice (overnight fasted, 7-9 weeks), at a dose of 10 mg/kg.

Two mice were set in each group and subjected to blood sampling alternatively, 4 to 5 time points per mouse. At 0.0833h (IV group only), 0.25 h, 0.5 h, 1.0 h, 2.0 h, 4.0 h, 6.0 h, 8.0 h, and 24 h after the intravenous or oral administration, about 30 μL of blood was collected by saphenous vein puncture and added into an anticoagulation tube with EDTA-K$_2$, and the plasma was isolated by centrifugation. The drug plasma concentration was determined by LC-MS/MS, and WinNonlin™ Version 6.3 (Pharsight, Mountain View, Calif.) pharmacokinetic software was used to calculate relevant pharmacokinetic parameters using the non-compartmental model linear logarithmic trapezoidal method.

The experimental results are shown in Table 6:

TABLE 6

Pharmacokinetic test results

| The test sample (compounds prepared in each example) | Clearance (mL/min/kg) | Half-life $T_{1/2}$ (h) | AUC$_{0-last}$ (nM · h) | Bioavailability F (%) |
|---|---|---|---|---|
| WX004B | 27.3 | 1.85 | 7211 | 66.7 |
| WX008B | 51.9 | 0.60 | 304 | 5.86 |
| WX009B | 92.1 | 0.61 | 40 | 1.26 |

Conclusion: The compounds of the present disclosure can significantly improve single or partial pharmacokinetic parameters in mouse.

Experimental Example 3: In Vivo Pharmacodynamic Study in NASH Mouse Model Induced by HFD+CCl$_4$ Objective of this Experiment:

The objective of this research is to study the effect of the compound on improving NASH and liver fibrosis in HFD+CCl$_4$ mouse model, with 1-181 as the reference compound. 1-181 is an Acetyl-CoA carboxylase inhibitor and is currently undergoing a phase II clinical study on non-alcoholic fatty liver disease (NAFLD). The HFD+CCl$_4$ mouse model used in this study is an animal model simulating human non-alcoholic fatty liver disease evolving into NASH, high-fat diet causes the fat accumulation and steatosis in liver cells; CCl$_4$ (intraperitoneal injection, twice a week) simulates the "second hit" of liver injury. This model is stable and reliable and has a high similarity to the pathogenesis of human NASH, it has the main pathological characteristics of NASH, including steatosis, apoptosis, inflammation and fibrosis, and also shows elevated plasma aminotransferase (ALT and AST) levels.

Experimental Design:

The modeling for this experiment included two steps of high-fat feed and CCl$_4$ induction. Firstly, the mice were fed with high-fat feed to induce non-alcoholic fatty liver, and mice with body weight >38 g were selected. The mice were continuously fed with high-fat feed, and simultaneously intraperitoneally injected with 25% CCl$_4$, 0.5 mg/kg, twice a week, for a total of four weeks. The day of starting CCl$_4$ administration was set as day 0, and the time of starting CCl$_4$ administration was set as hour 0. On the day of starting CCl$_4$ administration, the intragastric administration was started, and the administration volume of each group was 5 mL/kg, once a day for 4 weeks (28 days). The injection time of CCl$_4$ should be more than 4 hours away from the first drug administration time point in this day. 6 groups were set in this experiment, namely the healthy control group, model group, reference compound group (GS-0976), test compound group (WX004B, three doses). The healthy control group had 10 normal mice, which were fed with normal feed during the experiment, without CCl$_4$ injection; 50 obese mice were used in the model group and the administration group, 10 mice each group. After grouping, CCl$_4$ was injected intraperitoneally and the different doses of the drugs were administered. The grouping and dosage regimen are shown in Table 7.

TABLE 7

Animal grouping and dosing regimen

| Group | Number of animals | Test compound | Menstruum | Dosing regimen (dose \| mode of administration \| frequency \| total duration) | Feed and CCl$_4$ injection |
|---|---|---|---|---|---|
| Healthy control group | 10 | Menstruum | 40% polyethylene glycol/10% Solutol/50% water | 0\| Oral gavage\| QD \| Day 0-27 | Normal feed, without CCl$_4$ injection |
| Model group | 10 | Menstruum | 40% polyethylene glycol/10% Solutol/50% water | 0\| Oral gavage\| QD \|Day 0-27 | High-fat feed, CCl$_4$ injection |
| I-181, 3 mpk | 10 | I-181 | 40% polyethylene glycol/10% Solutol/50% water | 3 mg/kg\| Oral gavage\| QD \| Day 0-27 | High-fat feed, CCl$_4$ injection |
| WX004B, 0.5 mpk | 10 | WX004B | 40% polyethylene glycol/10% Solutol/50% water | 0.5 mg/kg\| Oral gavage\| QD \| Day 0-27 | High-fat feed, CCl$_4$ injection |
| WX004B, 1 mpk | 10 | WX004B | 40% polyethylene glycol/10% Solutol/50% water | 1 mg/kg\| Oral gavage\| QD \| Day 0-27 | High-fat feed, CCl$_4$ injection |
| WX004B, 3 mpk | 10 | WX004B | 40% polyethylene glycol/10% Solutol/50% water | 3 mg/kg\| Oral gavage\| QD \| Day 0-27 | High-fat feed, CCl$_4$ injection |

Experimental Results:

In the mouse model induced by the combination of a high-fat diet and $CCl_4$, WX004B achieves the same efficacy in both NAS and fibrosis as the reference compound at a higher dose.

What is claimed is:

1. A compound represented by formula (II), a stereoisomer or tautomer thereof, or a pharmaceutically acceptable salt thereof,

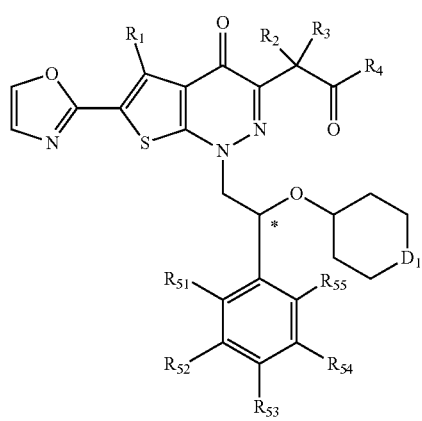

(II)

wherein, $D_1$ is selected from —O— and —N($R_6$)—;

$R_1$ is selected from H, F, Cl, Br, I, OH, $NH_2$ and $C_{1-3}$ alkyl, wherein the $C_{1-3}$ alkyl is optionally substituted by 1, 2 or 3 $R_a$;

$R_2$ is selected from H, F, Cl, Br, I, OH, $NH_2$ and $C_{1-6}$ alkyl, wherein the $C_{1-6}$ alkyl is optionally substituted by 1, 2 or 3 $R_b$;

$R_3$ is selected from H, F, Cl, Br, I and $C_{1-6}$ alkyl, wherein the $C_{1-6}$ alkyl is optionally substituted by 1, 2 or 3 $R_c$;

or, $R_2$ and $R_3$ are attached together to form a ring, the ring is selected from $C_{3-7}$ cycloalkyl and 4-7 membered heterocycloalkyl, the $C_{3-7}$ cycloalkyl and 4-7 membered heterocycloalkyl are optionally substituted by 1, 2 or 3 $R_d$;

$R_4$ is selected from OH, $NH_2$, $C_{1-3}$ alkyl and $C_{1-3}$ alkylamino, wherein the $C_{1-3}$ alkyl and $C_{1-3}$ alkylamino are optionally substituted by 1, 2 or 3 $R_e$;

each of $R_{51}$, $R_{52}$, $R_{53}$, $R_{54}$ and $R_{55}$ is independently selected from H, F, Cl, Br, I, OH, $NH_2$, $C_{1-6}$ alkyl, $C_{1-6}$ alkylamino and $C_{1-6}$ alkoxy, wherein the $C_{1-6}$ alkyl, $C_{1-6}$ alkylamino and $C_{1-6}$ alkoxy are optionally substituted by 1, 2 or 3 $R_f$;

$R_6$ is selected from H, $C_{1-6}$ alkyl, $C_{1-6}$ alkyl-C(=O)—, $C_{1-6}$ alkyl-S(=O)—, $C_{1-6}$ alkyl-S(=O)$_2$— and $C_{1-6}$ alkyl-O—C(=O)—, wherein the $C_{1-6}$ alkyl, $C_{1-6}$ alkyl-C(=O)—, $C_{1-6}$ alkyl-S(=O)—, $C_{1-6}$ alkyl-S(=O)$_2$— and $C_{1-6}$ alkyl-O—C(=O)— are optionally substituted by $R_g$;

each of $R_a$, $R_b$, $R_c$, $R_d$, $R_e$, $R_f$ and $R_g$ are independently selected from F, Cl, Br, I, OH, $NH_2$ and $C_{1-3}$ alkyl, wherein the $C_{1-3}$ alkyl is optionally substituted by 1, 2 or 3 R;

each R is independently selected from F, Cl, Br, I, OH and $NH_2$;

the 4-7 membered heterocycloalkyl contains 1, 2, 3 or 4 heteroatoms or heteroatomic groups independently selected from —NH—, —O—, —S— and N;

the carbon atom labeled with "*" is a chiral carbon atom, and exists in the form of (R) or (S) single enantiomer or enriched in one enantiomer.

2. The compound, the stereoisomer or tautomer thereof, or the pharmaceutically acceptable salt thereof as defined in claim 1, wherein, each of $R_a$, $R_b$, $R_c$, $R_d$, $R_e$, $R_f$ and $R_g$ is independently selected from F, Cl, Br, I, OH, and $NH_2$.

3. The compound, the stereoisomer or tautomer thereof, or the pharmaceutically acceptable salt thereof as defined in claim 1, wherein, $R_1$ is selected from H, F, Cl, Br, I, OH, $NH_2$ and $CH_3$.

4. The compound, the stereoisomer or tautomer thereof, or the pharmaceutically acceptable salt thereof as defined in claim 1, wherein, $R_2$ is selected from H, F, Cl, Br, I, OH, $NH_2$, $CH_3$ and Et.

5. The compound, the stereoisomer or tautomer thereof, or the pharmaceutically acceptable salt thereof as defined in claim 1, wherein, $R_3$ is selected from H, F, Cl, Br, I, $CH_3$ and Et.

6. The compound, the stereoisomer or tautomer thereof, or the pharmaceutically acceptable salt thereof as defined in claim 1, wherein, $R_2$ and $R_3$ are attached together to form a ring, the ring is selected from $C_{3-6}$ cycloalkyl and 5-6 membered heterocycloalkyl, the $C_{3-6}$ cycloalkyl and 5-6 membered heterocycloalkyl are optionally substituted by 1, 2 or 3 $R_d$.

7. The compound, the stereoisomer or tautomer thereof, or the pharmaceutically acceptable salt thereof as defined in claim 6, wherein, $R_2$ and $R_3$ are attached together to form a ring, the ring is selected from cyclopropyl, cyclobutyl, cyclopentyl, cyclohexyl, tetrahydrofuranyl, tetrahydropyranyl and piperidinyl, wherein the cyclopropyl, cyclobutyl, cyclopentyl, cyclohexyl, tetrahydrofuranyl, tetrahydropyranyl and piperidinyl are optionally substituted by 1, 2 or 3 $R_d$.

8. The compound, the stereoisomer or tautomer thereof, or the pharmaceutically acceptable salt thereof as defined in claim 7, wherein, $R_2$ and $R_3$ are attached together to form a ring, the ring is selected from

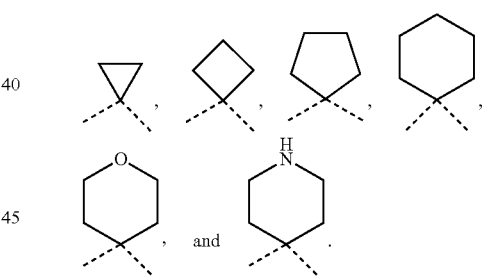

9. The compound, the stereoisomer or tautomer thereof, or the pharmaceutically acceptable salt thereof as defined in claim 1, wherein, $R_4$ is selected from OH and $NH_2$.

10. The compound, the stereoisomer or tautomer thereof, or the pharmaceutically acceptable salt thereof as defined in claim 1, wherein, each of $R_{51}$, $R_{52}$, $R_{53}$, $R_{54}$ and $R_{55}$ is independently selected from H, F, Cl, Br, I, OH, $NH_2$, $C_{1-3}$ alkyl, $C_{1-3}$ alkylamino and $C_{1-3}$ alkoxy, wherein the $C_{1-3}$ alkyl, $C_{1-3}$ alkylamino and $C_{1-3}$ alkoxy are optionally substituted by 1, 2 or 3 $R_f$.

11. The compound, the stereoisomer or tautomer thereof, or the pharmaceutically acceptable salt thereof as defined in claim 10, wherein, each of $R_{51}$, $R_{52}$, $R_{53}$, $R_{54}$ and $R_{55}$ is independently selected from H, F, Cl, Br, I, OH, $NH_2$, $CH_3$, Et and

12. The compound, the stereoisomer or tautomer thereof, or the pharmaceutically acceptable salt thereof as defined in claim 1, wherein, $R_6$ is selected from H, $C_{1-3}$ alkyl, $C_{1-3}$ alkyl-C(=O)—, $C_{1-3}$ alkyl-S(=O)—, $C_{1-3}$ alkyl-S(=O)$_2$— and $C_{1-4}$ alkyl-O—C(=O)—, wherein the $C_{1-3}$ alkyl, $C_{1-3}$ alkyl-C(=O)—, $C_{1-3}$ alkyl-S(=O)—, $C_{1-3}$ alkyl-S(=O)$_2$— and $C_{1-4}$ alkyl-O—C(=O)— is optionally substituted by $R_g$.

13. The compound, the stereoisomer or tautomer thereof, or the pharmaceutically acceptable salt thereof as defined in claim 12, wherein, $R_6$ is selected from H, $CH_3$, $CH_3$—C(=O)—, $CH_3$—S(=O)$_2$—, $CH_3$—O—C(=O)— and

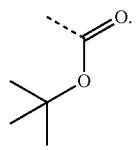

14. The compound, the stereoisomer or tautomer thereof, or the pharmaceutically acceptable salt thereof as defined in claim 1, wherein the compound is selected from

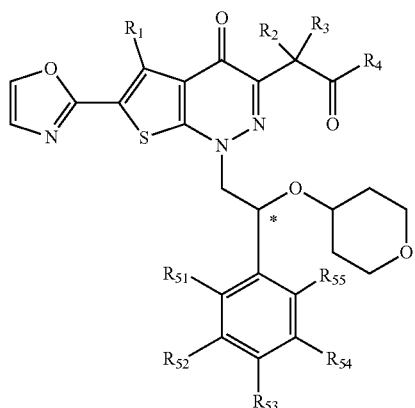

(I)

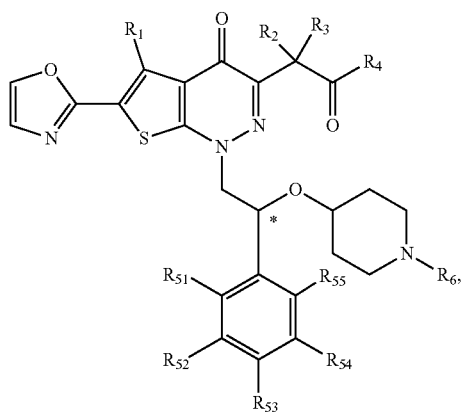

(II-1)

wherein,
$R_1$, $R_4$, $R_{51}$, $R_{52}$, $R_{53}$, $R_{54}$ and $R_{55}$ and $R_6$ are as defined in claim 1;
the carbon atom labeled with "*" is a chiral carbon atom, and exists in the form of (R) or (S) single enantiomer or enriched in one enantiomer.

15. The compound, the stereoisomer or tautomer thereof, or the pharmaceutically acceptable salt thereof as defined in claim 1, wherein the compound is selected from

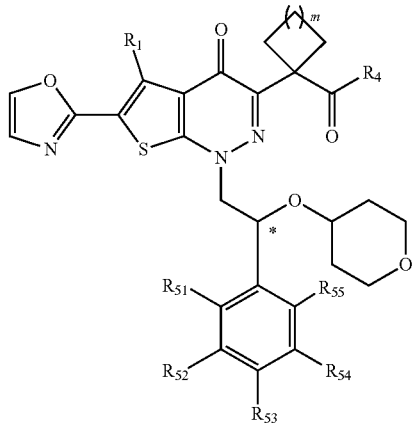

(I-1)

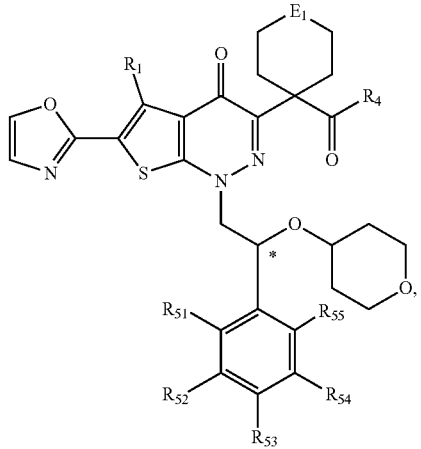

(I-2)

wherein,
m is 0, 1, 2 or 3;
$E_1$ is —O— or —NH—;
$R_1$, $R_4$, $R_{51}$, $R_{52}$, $R_{53}$, $R_{54}$ and $R_{55}$ are as defined in claim 1;
the carbon atom labeled with "*" is a chiral carbon atom, and exists in the form of (R) or (S) single enantiomer or enriched in one enantiomer.

16. The compound, the stereoisomer or tautomer thereof, or the pharmaceutically acceptable salt thereof as defined in claim 15, wherein the compound is selected from

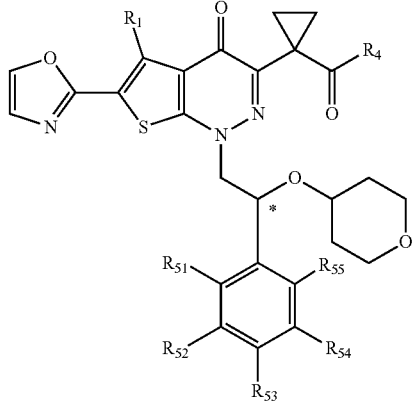

(I-1A)

-continued
(I-1B)
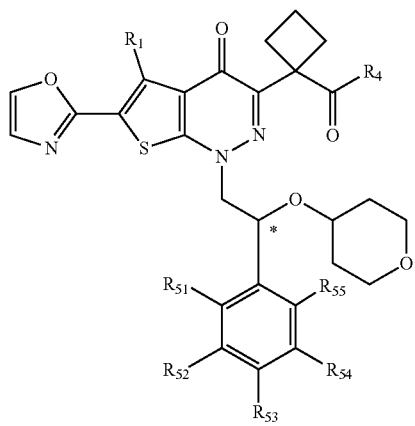
(I-1C)
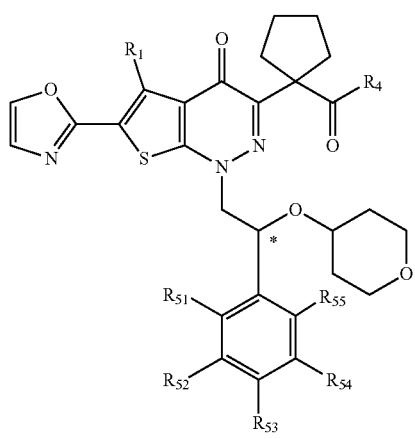
(I-1D)
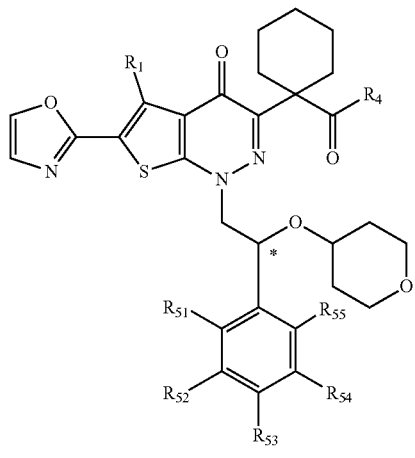
wherein,
$R_1$, $R_4$, $R_{51}$, $R_{52}$, $R_{53}$, $R_{54}$ and $R_{55}$ are as defined in claim 15;
the carbon atom labeled with "*" is a chiral carbon atom, and exists in the form of (R) or (S) single enantiomer or enriched in one enantiomer.
17. A compound represented by the following formula, a stereoisomer or tautomer thereof, or a pharmaceutically acceptable salt thereof,
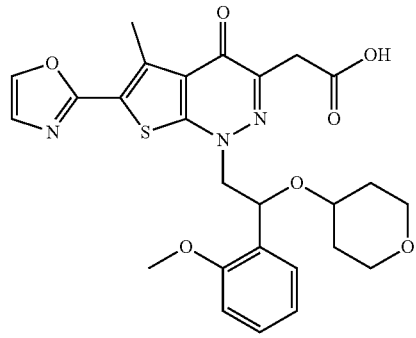
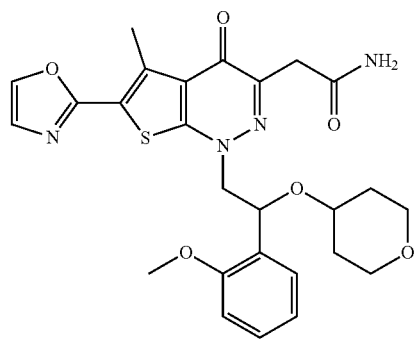
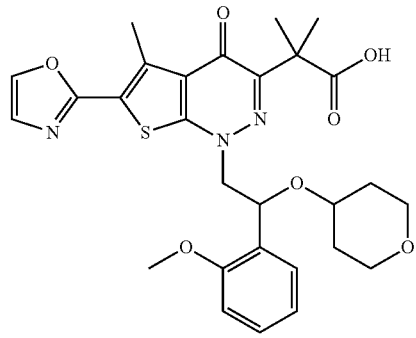
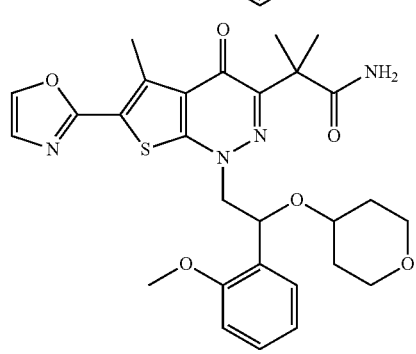
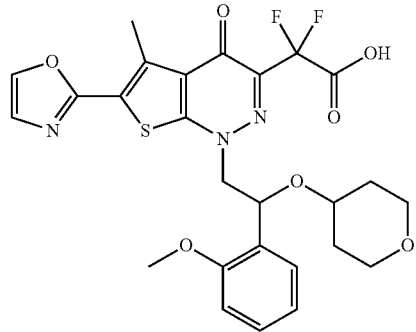

71
-continued
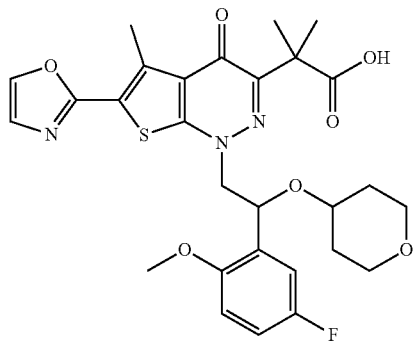
72
-continued
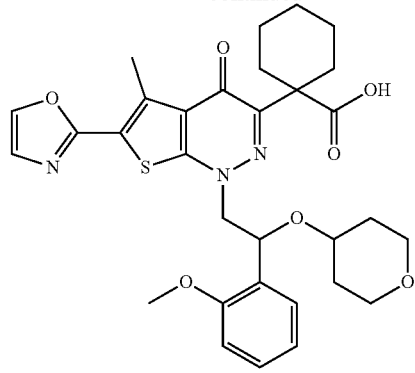
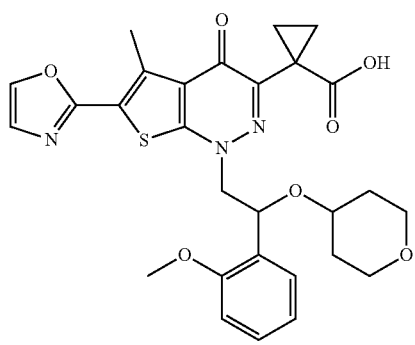
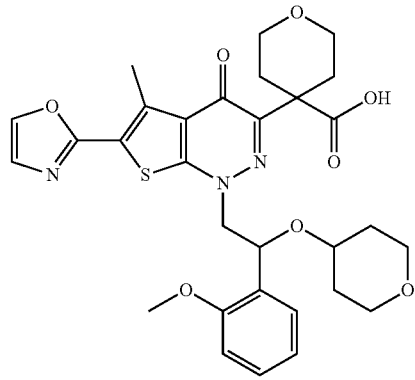
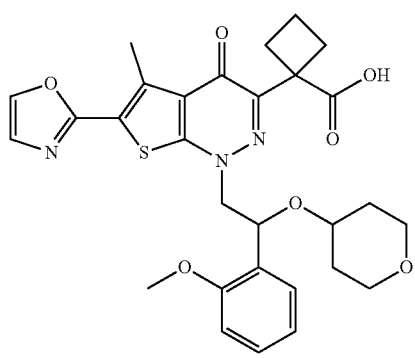
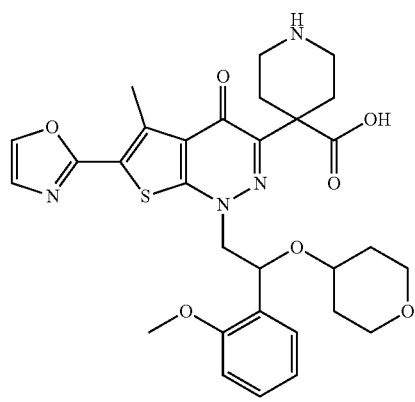
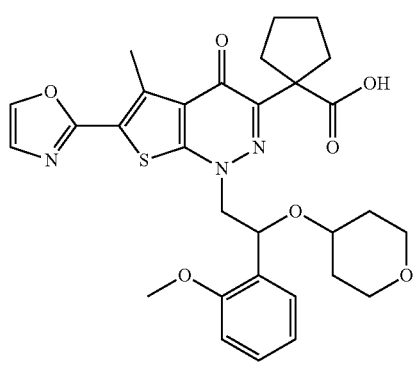
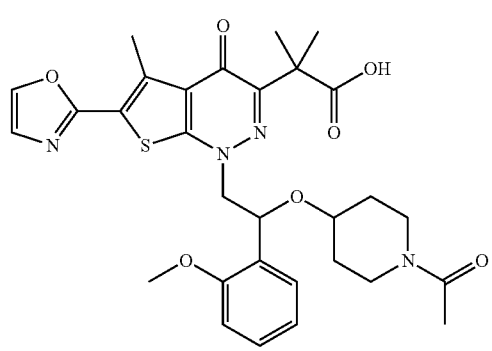

73
-continued
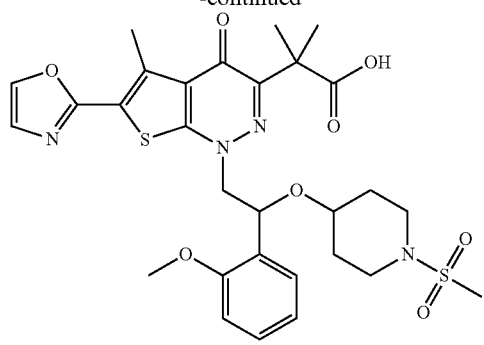
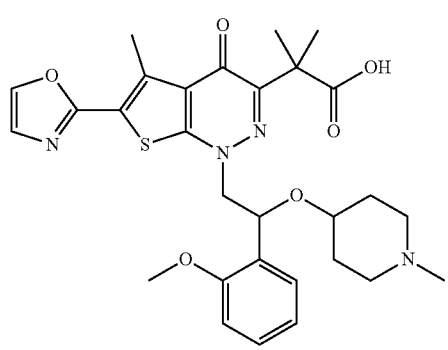
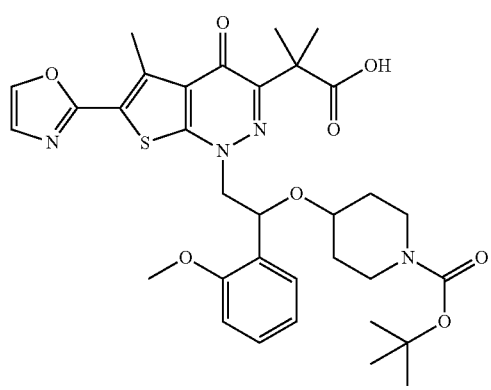
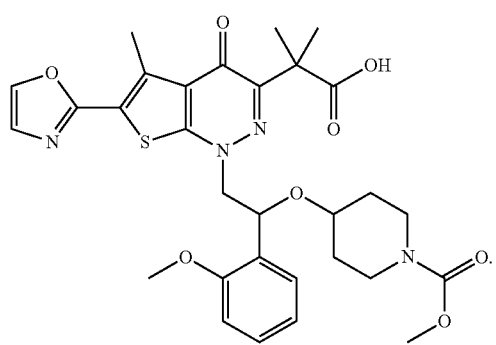
18. The compound, the stereoisomer or tautomer thereof, or the pharmaceutically acceptable salt thereof as defined in claim 17,
74
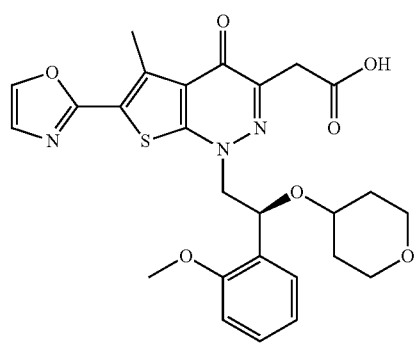
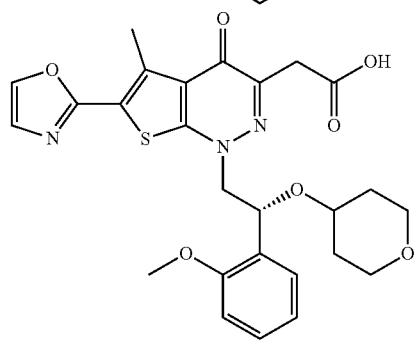
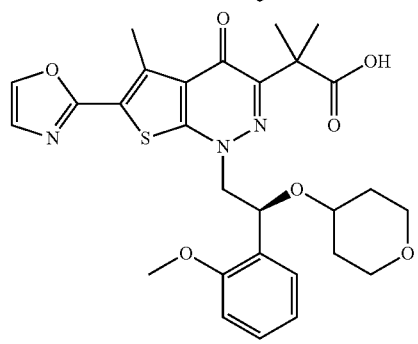
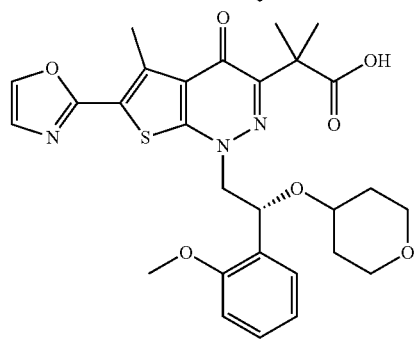
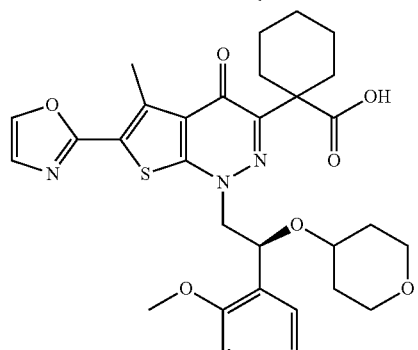

75
-continued
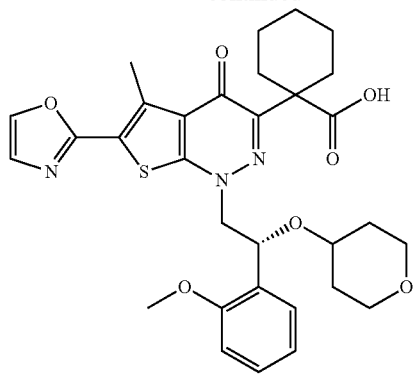
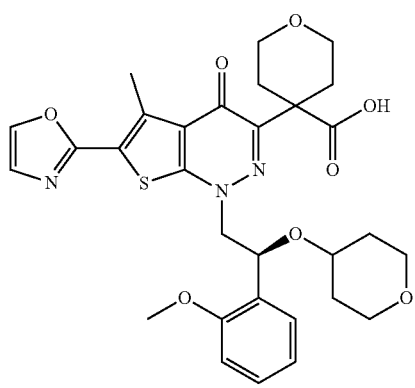
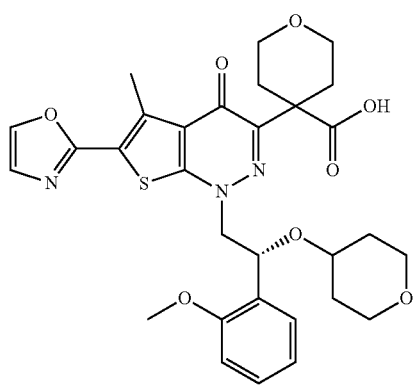
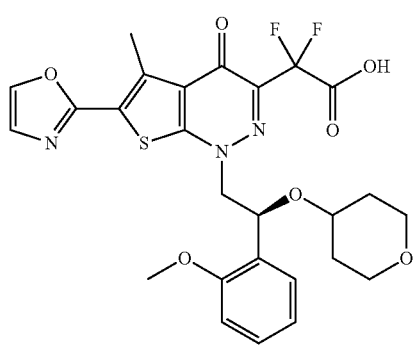
76
-continued
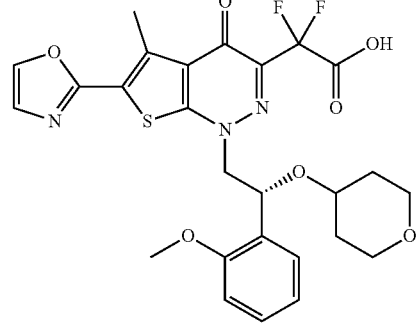
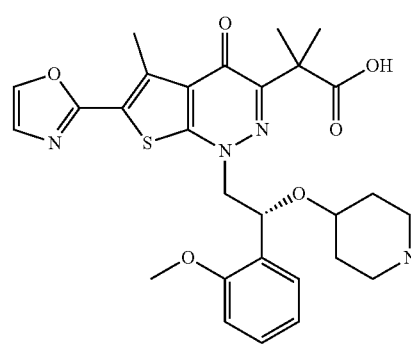
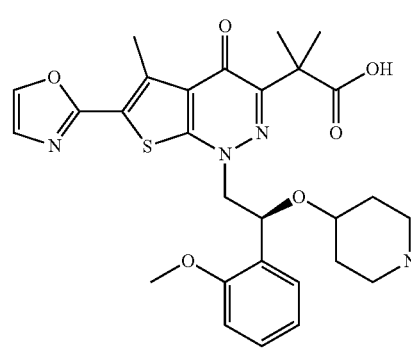
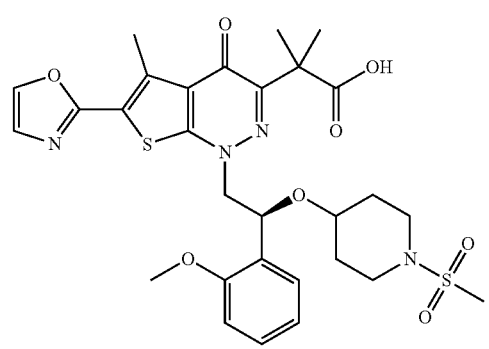

77

-continued

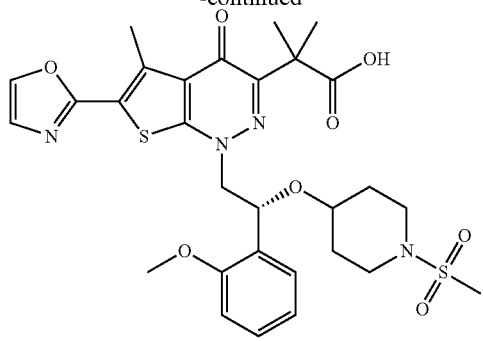

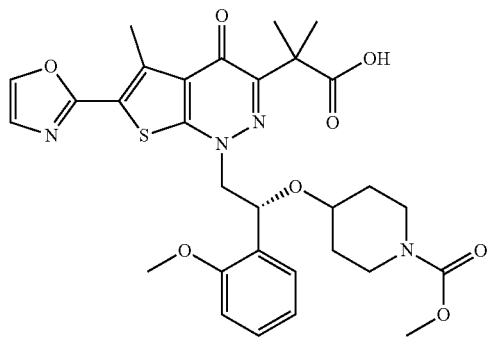 [SMILES: COC(=O)N1CCC(O[C@@H](Cn2nc(C(C)(C)C(=O)O)c(=O)c3c(C)c(-c4ncco4)sc32)c2ccccc2OC)CC1]

78

-continued

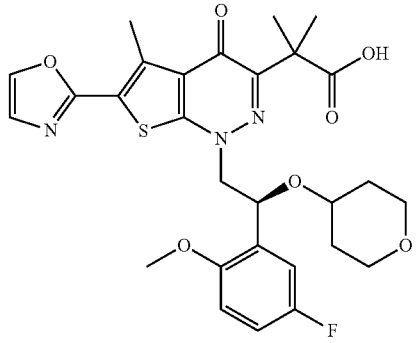

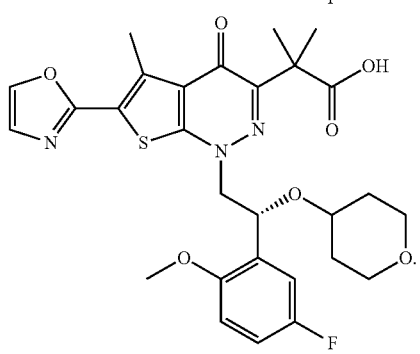

19. A method for inhibiting ACC1 and/or ACC2 in a subject in need thereof, comprising administering the compound, the stereoisomer or tautomer thereof, or the pharmaceutically acceptable salt thereof as defined in claim 1 to the subject.

20. A method for treating non-alcoholic steatohepatitis and liver fibrosis in a subject in need thereof, comprising administering the compound, the stereoisomer or tautomer thereof, or the pharmaceutically acceptable salt thereof as defined in claim 1 to the subject.

\* \* \* \* \*